(12) United States Patent
Ziemba

(10) Patent No.: US 8,613,617 B2
(45) Date of Patent: *Dec. 24, 2013

(54) ULTRASONIC DENTAL TOOL HAVING A LIGHT SOURCE

(75) Inventor: Steven L. Ziemba, Fullerton, CA (US)

(73) Assignee: Zila, Inc., Fort Collins, CO (US)

( * ) Notice: Subject to any disclaimer, the term of this patent is extended or adjusted under 35 U.S.C. 154(b) by 61 days.

This patent is subject to a terminal disclaimer.

(21) Appl. No.: 13/021,941

(22) Filed: Feb. 7, 2011

(65) Prior Publication Data

US 2011/0159454 A1   Jun. 30, 2011

Related U.S. Application Data

(63) Continuation of application No. 11/929,377, filed on Oct. 30, 2007, now Pat. No. 8,491,300, which is a continuation of application No. 11/357,576, filed on Feb. 17, 2006, now abandoned.

(60) Provisional application No. 60/654,306, filed on Feb. 17, 2005, provisional application No. 60/661,722, filed on Mar. 14, 2005.

(51) Int. Cl.
    *A61C 1/00* (2006.01)

(52) U.S. Cl.
    USPC .......................................................... 433/29

(58) Field of Classification Search
    USPC ........ 433/86, 119; 128/200.16; 451/165, 910; 318/116, 118; 604/22; 606/169, 171, 606/177, 178
    See application file for complete search history.

(56) References Cited

U.S. PATENT DOCUMENTS

| 3,706,514 A | 12/1972 | Ruf |
| 4,069,444 A | 1/1978 | Heim |
| 4,148,309 A | 4/1979 | Reibel |
| 4,840,563 A | 6/1989 | Altendorf |
| 4,900,252 A | 2/1990 | Liefke |
| 5,185,004 A | 2/1993 | Lashinski |
| 5,267,860 A | 12/1993 | Ingram et al. |
| 5,275,607 A * | 1/1994 | Lo et al. ................ 606/169 |
| 5,382,162 A | 1/1995 | Sharp |

(Continued)

FOREIGN PATENT DOCUMENTS

| DE | 3422628 | 12/1985 |
| DE | 3706934 | 9/1988 |

(Continued)

*Primary Examiner* — Robyn Doan
*Assistant Examiner* — Matthew Nelson
(74) *Attorney, Agent, or Firm* — Jeffer Mangels Butler & Mitchell LLP

(57) ABSTRACT

An ultrasonic dental insert having at least one light source. A first transducer generates ultrasonic vibrations. A connecting body has a proximal end and a distal end having a tip attached thereto. The proximal end is attached to the first transducer so as to receive the ultrasonic vibrations therefrom and to transmit the ultrasonic vibrations toward the tip attached to the distal end. A second transducer is disposed substantially proximate to the connecting body for generating a voltage signal in response to movement of a portion of the connecting body according to the ultrasonic vibrations. A magnetic material including a source of a magnetic field is present in close proximity to the insert. At least one light source substantially proximate to the tip is connected to and receives the voltage signal from the second transducer to generate light. The ultrasonic dental insert may be inserted into a handpiece for providing electromagnetic energy to the first transducer to generate the ultrasonic vibrations.

21 Claims, 13 Drawing Sheets

(56) References Cited

U.S. PATENT DOCUMENTS

| | | |
|---|---|---|
| 5,476,379 A | 12/1995 | Disel |
| 5,655,906 A * | 8/1997 | Coss et al. .................... 433/115 |
| 5,758,650 A * | 6/1998 | Miller et al. .................. 600/461 |
| 5,927,977 A | 7/1999 | Sale et al. |
| 6,086,369 A * | 7/2000 | Sharp et al. .................... 433/118 |
| 6,095,810 A * | 8/2000 | Bianchetti ........................ 433/29 |
| 6,386,866 B1 * | 5/2002 | Hecht et al. ..................... 433/29 |
| 6,503,081 B1 | 1/2003 | Feine |
| 6,616,446 B1 | 9/2003 | Schmid |
| 6,716,028 B2 | 4/2004 | Rahman et al. |
| 6,735,802 B1 | 5/2004 | Lundell et al. |
| 6,899,538 B2 | 5/2005 | Matoba |
| 6,955,536 B1 | 10/2005 | Buchanan |
| 6,994,546 B2 | 2/2006 | Fischer et al. |
| 7,104,794 B2 | 9/2006 | Levy |
| 7,596,827 B1 | 10/2009 | Puneet |
| 2002/0088068 A1 | 7/2002 | Levy |
| 2004/0185412 A1 * | 9/2004 | Feine .............................. 433/29 |
| 2004/0255409 A1 | 12/2004 | Hilscher et al. |
| 2004/0259054 A1 | 12/2004 | Mayer |
| 2005/0032017 A1 * | 2/2005 | Levy ............................... 433/29 |
| 2005/0050658 A1 | 3/2005 | Chan et al. |
| 2006/0154209 A1 | 7/2006 | Hayman et al. |
| 2006/0234185 A1 | 10/2006 | Ziemba |
| 2006/0269900 A1 | 11/2006 | Paschke et al. |
| 2007/0011836 A1 | 1/2007 | Brewer et al. |
| 2007/0031782 A1 | 2/2007 | Warner et al. |

FOREIGN PATENT DOCUMENTS

| | | |
|---|---|---|
| DE | 4340598 | 1/1995 |
| DE | 2356311 | 5/2001 |
| FR | 2881341 | 4/2006 |
| WO | 2005/002458 | 1/2005 |
| WO | 2005053561 | 6/2005 |
| WO | 2006089104 | 8/2006 |
| WO | 2006125066 | 11/2006 |

\* cited by examiner

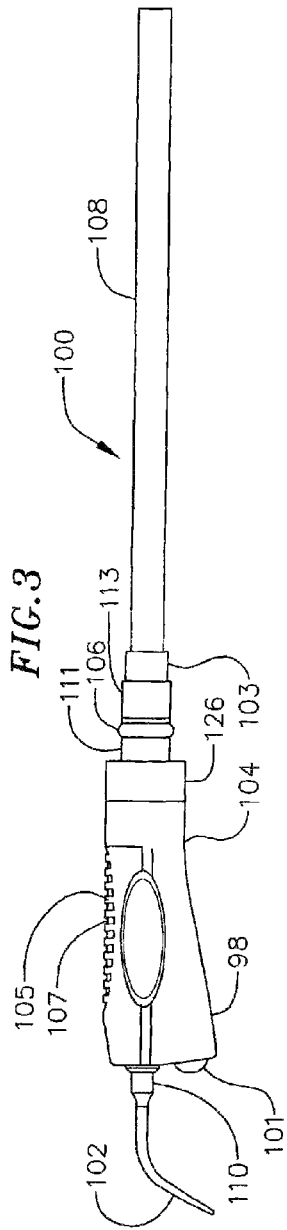
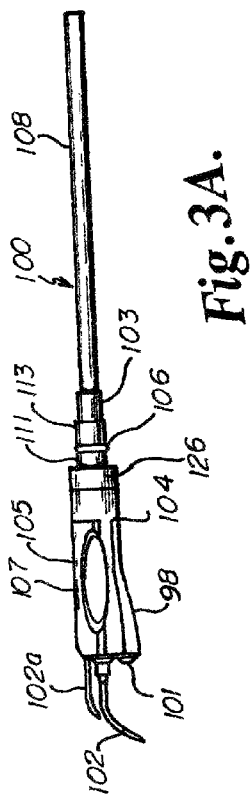
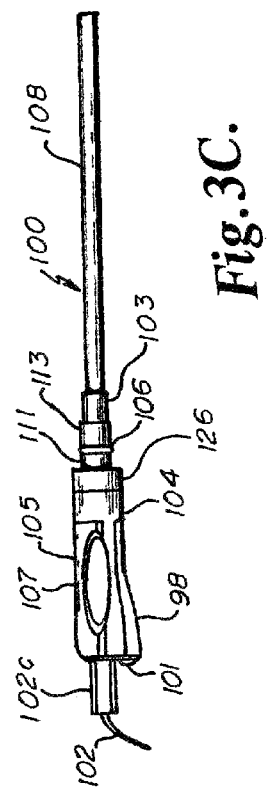

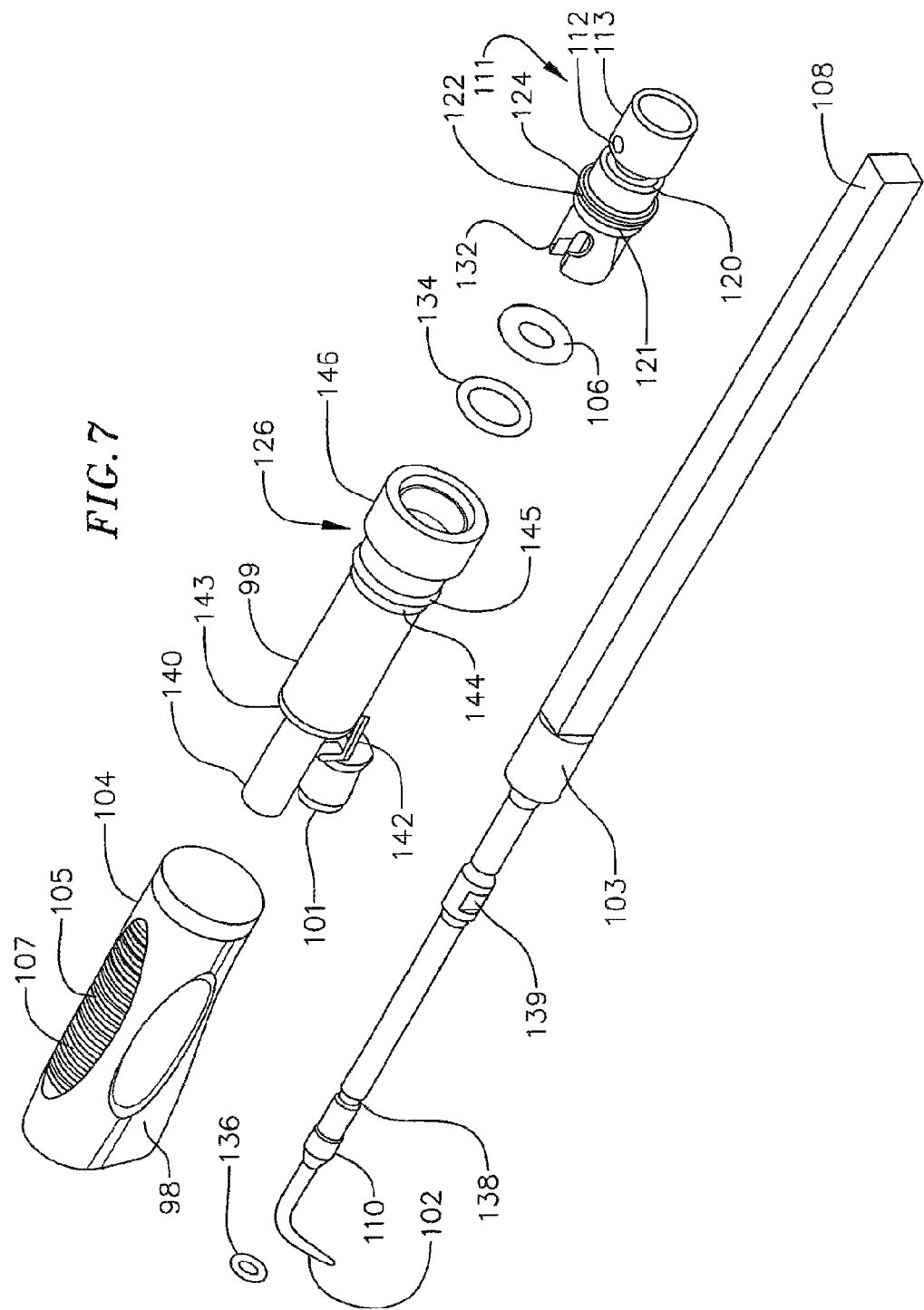

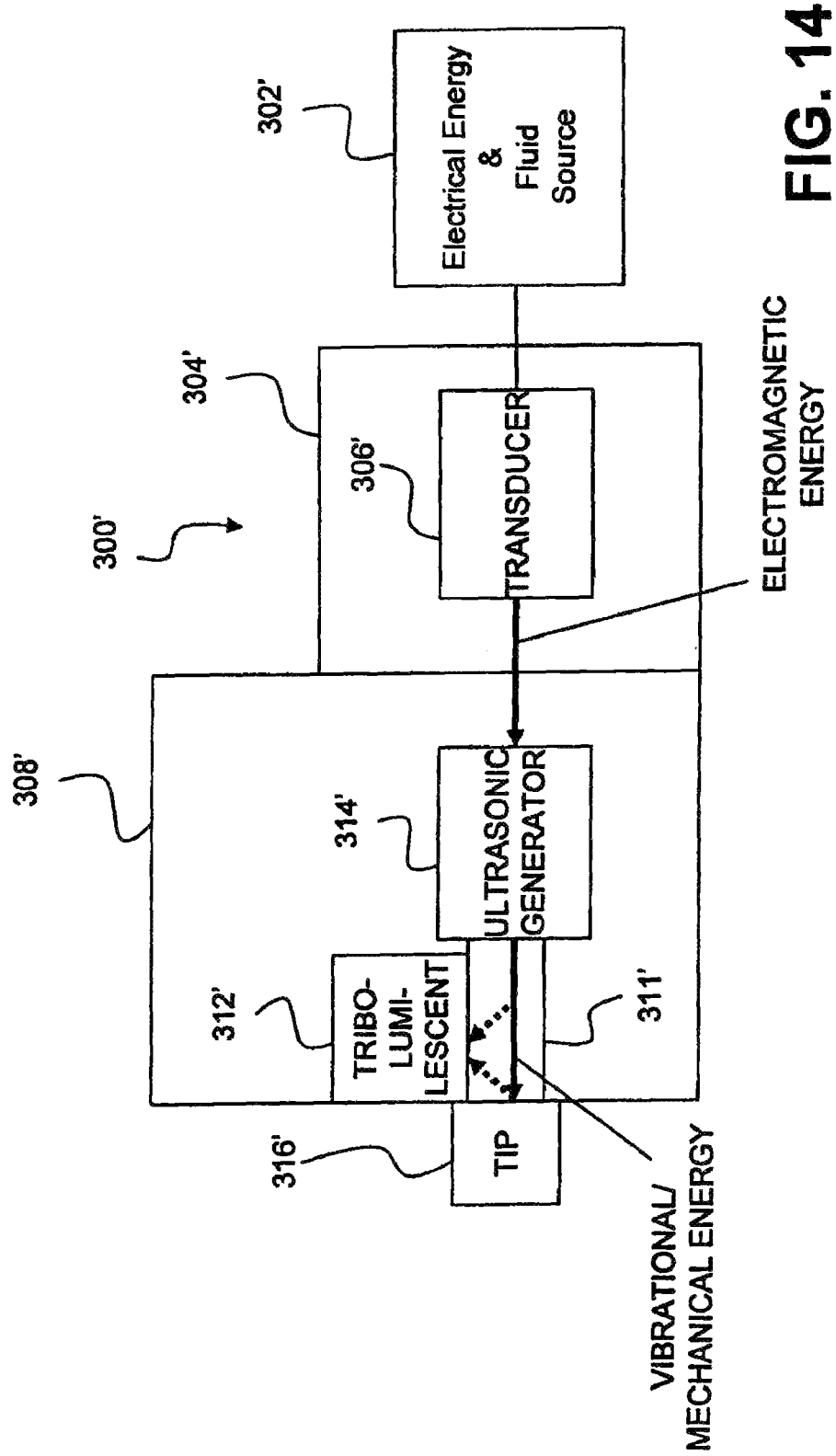

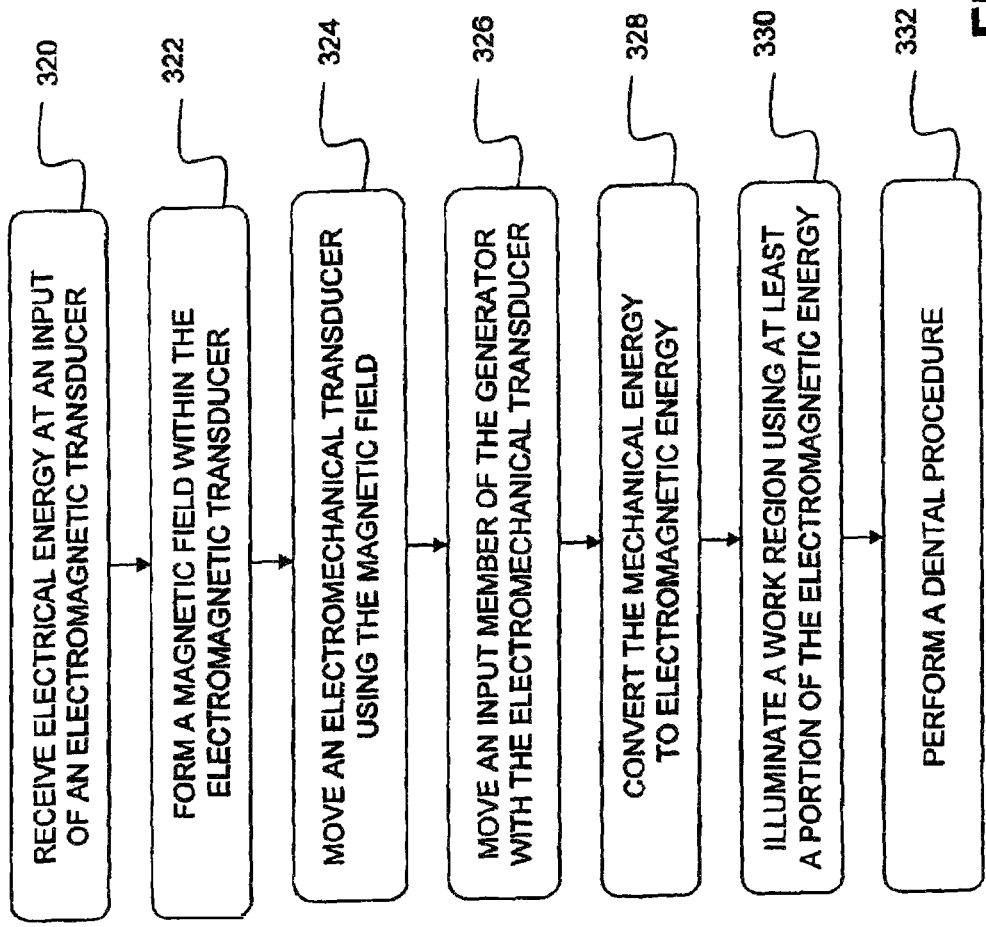

ULTRASONIC DENTAL TOOL HAVING A LIGHT SOURCE

CROSS-REFERENCE TO RELATED APPLICATIONS

This application is a continuation of U.S. patent application Ser. No. 11/929,377, filed on Oct. 30, 2007, which is a continuation of U.S. patent application Ser. No. 11/357,576, filed on Feb. 17, 2006, which claims the benefit of U.S. provisional patent application Ser. No. 60/654,306, filed Feb. 17, 2005, entitled "Ultrasonic Dental Tool having a Light Source", the content of which is hereby incorporated by reference.

FIELD OF THE INVENTION

The present invention is related to ultrasonic dental tools, and more particularly to an ultrasonic dental tool having a light source.

BACKGROUND

Dental practitioners use ultrasonic dental tools (instruments) for dental treatments and procedures, such as scaling, periodontal treatments, root canal therapy, and the like. An ultrasonic dental tool typically includes a handpiece coupled at one end (i.e., a proximal end) to an electrical energy source and a fluid source via a cable. The cable includes a hose to provide a fluid (e.g., water), and conductors to provide electrical energy.

The other end (i.e., a distal end) of the handpiece has an opening intended to receive a replaceable insert with a transducer (e.g., a magnetostrictive transducer) carried on the insert. The transducer extends from a proximal end of the insert into a hollow interior of the handpiece. An ultrasonically vibrated tip extends from a distal end of the insert.

Since a patient's mouth is a small space in which to work, it is often difficult to see well into all regions of the mouth under the best of conditions. When a dental practitioner can not see clearly in the field of work, it is more likely that painful slips can occur. The often sharp implements, vibrating at ultrasonic frequencies, may do considerable harm to soft tissue (such as gum tissue) resulting in bleeding and pain.

The large and focused lamp that hangs over the field of work while the dental practitioner uses ultrasonic dental tools in the patient's mouth often becomes obscured when the dental practitioner leans closely toward the patient to work in confined spaces within the mouth. The suddenly darker field is more difficult in which to work accurately. Small slips and injuries can result.

Therefore, it is desirable to provide an ultrasonic dental tool that can bring light directly into the field of work (i.e., patient's mouth). If such light can be provided using a source of energy already available in existing ultrasonic dental generating units, circuit complexity and energy requirements can be reduced.

SUMMARY OF THE INVENTION

The present invention relates to an ultrasonic dental insert having at least one light source and at least one magnetic material in close proximity for increasing and/or maintaining the brightness of the output light from the light source when in use. The dental insert includes a first transducer for generating ultrasonic vibrations and a connecting body having a proximal end and a distal end. The distal end has a tip attached thereto. The proximal end is attached to the first transducer so as to receive the ultrasonic vibrations therefrom and to transmit the ultrasonic vibrations toward the tip attached to the distal end. The ultrasonic dental insert may also include a hand grip portion and may be inserted into a handpiece for providing electromagnetic energy to the first transducer to generate the ultrasonic vibrations, to form an ultrasonic dental tool having a light source.

In an exemplary embodiment, a second transducer may be disposed on the insert, for example, proximate to the connecting body, and generates a voltage signal in response to movement of a portion of the connecting body according to the ultrasonic vibrations. At least one light source, substantially proximate to the tip, may be connected to and receives the voltage signal from the second transducer to generate light. The dental insert and/or handpiece includes a magnetic material or a magnetic source in close proximity for initiating, re-establishing, increasing and/or maintaining the brightness of the output light from the light source when in use.

A magnetic material or a magnetic source, for example, a magnet, may be used to initiate and/or re-establish proper magnetization of the metal connecting body for the purpose of allowing the connecting body to generate an electromagnetic field during operation of the insert.

In one embodiment, a magnetic material may be placed inside an appropriate holder and may be used to magnetize or re-magnetize an insert and tip to allow the connecting body to generate an electromagnetic field during operation of the insert and tip.

In another embodiment, a magnetic material or magnetic source may be used to fashion at least a portion of the insert and/or the connecting body.

In a further embodiment, the magnetic material or source, such as a magnet, may be placed in the hand grip portion of the insert, to enable the connecting body, once magnetized, to retain its magnetic properties in an optimal manner even after exposure to heat or physical shock.

The present invention also relates to an ultrasonic dental tool that includes an ultrasonic dental insert inserted into a handpiece having a hand grip portion. The ultrasonic dental insert includes a first transducer for generating ultrasonic vibrations and a connecting body having a proximal end and a distal end having a tip attached thereto. The proximal end is attached to the first transducer so as to receive the ultrasonic vibrations therefrom and to transmit the ultrasonic vibrations toward the tip attached to the distal end.

A second transducer, for example, may be likewise disposed on the insert, proximate to the connecting body and may generate a voltage signal in response to movement of a portion of the connecting body according to the ultrasonic vibrations. At least one light source substantially proximate to the tip may be connected to receive the voltage signal from the second transducer to generate light.

A magnetic material or magnetic field source may be disposed in close proximity to the dental insert for increasing and/or maintaining the brightness of the output light from the light source when in use. A magnetic material or magnetic source, for example, a permanent magnet, may also be used to initiate and then re-establish proper magnetization of the metal connecting body for the purpose of allowing the connecting body to generate an electromagnetic field during operation of the insert.

In one embodiment, a magnetic material or magnetic source, such as a permanent magnet, may be placed inside an appropriate holder and used to magnetize or remagnetize an insert and tip to allow the connecting body to generate an electromagnetic field during operation of the insert and tip.

In another embodiment, a magnetic material or source may be used to fashion at least a portion of the insert and/or the connecting body.

In a further embodiment, the magnetic material or source, such as a magnet, may be placed in the handpiece, to enable the connecting body, once magnetized, to retain its magnetic properties in an optimal manner even after exposure to heat or physical shock.

The present invention further relates to an ultrasonic dental insert including a motor, a work tip, and a coupling member disposed between said motor and said work tip, said coupling member being adapted to receive mechanical energy from said motor. An electrical generator may be mechanically coupled to said coupling member, said electrical generator being adapted to receive a portion of said mechanical energy from said coupling member. An electrical conductor has a first end electrically coupled to said electrical generator. At least one light source has an electrical input electrically coupled to a second end of said electrical conductor.

In one embodiment, the motor may be a magnetostrictive transducer. In another embodiment, the motor may be a piezoelectric transducer.

The dental insert may include a magnetic material or source in close proximity for increasing and/or maintaining the brightness of the output light from the light source when in use. A magnetic material or source, for example, a magnet, may be used to initiate and then re-establish proper magnetization of the coupling member for allowing the coupling member to generate an electromagnetic field during operation of the insert.

In one embodiment, a magnetic material or source may be placed inside an appropriate holder and used to magnetize or re-magnetize an insert and tip to allow the coupling member to generate an electromagnetic field during operation of the insert and tip.

In another embodiment, a magnetic material may be used to fashion at least a portion of the insert and/or the coupling member.

In a further embodiment, the dental insert may also include a handgrip, and the magnetic material, such as a magnet, may be placed in the hand grip portion of the insert, to enable the connecting body, once magnetized, to retain its magnetic properties in an optimal manner even after exposure to heat or physical shock.

In one aspect of the present invention, a voltage regulating device may be employed to modulate the electrical energy input into the at least one light source to minimize input voltage fluctuations to the light source. In one aspect, the voltage regulating device may include a zener diode for clamping the input voltage at a specific value to minimize fluctuations.

BRIEF DESCRIPTION OF THE DRAWINGS

These and other aspects of the invention may be understood by reference to the following detailed description, taken in conjunction with the accompanying drawings, wherein:

FIG. 3 is a side view of the dental tool insert of FIG. 2, which has been rotated by approximately 90 degrees from the perspective view depicted in FIG. 2;

FIG. 3A is a side view of a dental tool insert having an external flow tube for delivering water to the tip in an alternative embodiment of the present invention;

FIG. 3C illustrates a side view of a dental tool insert having a sleeve covering portions of the insert;

FIG. 7 is an exploded perspective view of the dental tool insert of FIG. 2;

FIG. 14 is a block diagram of another ultrasonic dental unit (or system) including a triboluminescent material; and FIG. 15 is a flow diagram illustrating a method of illuminating a work region using the ultrasonic dental tool in exemplary embodiments of the present invention.

DETAILED DESCRIPTION

The detailed description set forth below is intended as a description of the presently exemplified embodiment in accordance with aspects of the present invention and is not intended to represent the only forms in which the present invention may be prepared or utilized. It is to be understood, however, that the same or equivalent functions and features may be accomplished by different embodiments that are also intended to be encompassed within the spirit and scope of the invention.

Unless defined otherwise, all technical and scientific terms used herein have the same meaning as commonly understood to one of ordinary skill in the art to which this invention belongs. Although any methods, devices and materials similar or equivalent to those described herein may be used in the practice or testing of the invention, the exemplified methods, devices and materials are now described.

In exemplary embodiments of the present invention, an ultrasonic dental insert has at least one integrated light source such as a semiconductor light emitting device; a light-emitting chip such as a light emitting diode (LED) which may be a solid state LED; a visible light emitting diode (VLED); an LED array; and so on, that enables a dental practitioner to cast light on the work field while applying a tool to the teeth. The dental insert includes a magnetic material or source in close proximity to the insert and/or the connecting body for initiating, re-establishing, increasing and/or maintaining proper magnetization of the connecting body. This in turn may lead to initiating, re-establishing, increasing and/or maintaining the brightness of the output light from the LED when in use. In one aspect, the integrated light source may be dimensionally small so that it may be easily integrated into the insert.

The light source is energized by the already available ultrasonic vibrational energy such that an additional source of energy is not needed. By way of example, a transducer such as and/or including, an illumination energy coil, is provided and attached to the light source such that the light source is energized using vibrational energy converted by the transducer. By way of example, a first transducer is used to generate ultrasonic vibrations. This causes the connecting body to move rapidly to generate an electromagnetic field during operation of the insert. As the connecting body of the dental insert moves, an alternating current (ac) voltage is generated in the illumination energy coil, which is connected in series with the light source (e.g., light emitting diode (LED)) to provide energy for light emission. In other embodiments, any other suitable transducer for converting vibrational energy to energy for light emission may be used. The word "light source" as used herein may include one or more than one light source(s).

Figure 1:
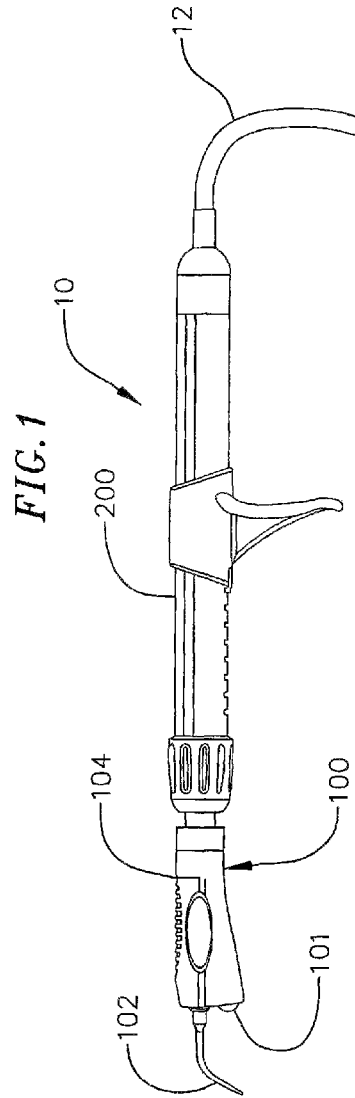
FIG. 1 illustrates an ultrasonic dental unit (or system) including an ultrasonic dental tool attached to an electrical energy & fluid source.

FIG. 1 illustrates an ultrasonic dental unit including an ultrasonic dental tool 10 attached to an electrical energy & fluid source 14 via a cable 12. The cable 12 includes a conduit for carrying fluid as well as wires for carrying electrical signals from the electrical energy & fluid source 14 to the ultrasonic dental tool 10. The ultrasonic dental tool 10 includes a handpiece 200 and an insert 100 adapted to be inserted into the handpiece 200. The insert 100 includes a housing 104, a portions thereof may also be used as, for example, a handgrip, also denoted as 104. The insert 100 may have an O-ring 106 mounted thereon for engaging and pressing against the inner surface of the handpiece 200 so as to form a water tight seal, as exemplified in FIG. 2 or 3 below.

It can be seen in FIG. 1 that a light source 101 is integrated with the insert 100 near its distal end, substantially proximate to a tip 102. In another embodiment, a plurality of light sources 101 (not specifically shown), may be integrated with the insert 100 near the distal end. In other embodiments, the light source 101 may include two or more lights (such as LEDs 151 and 161 shown in FIGS. 3B and 10). In still other embodiments, the light source 101 may not be integrated with the insert 100, but may instead be non-integrally attached to the insert 100 and/or the hand grip 104, or only one light source 101 is integrated with the insert 100 and additional ones are not.

Figure 2:
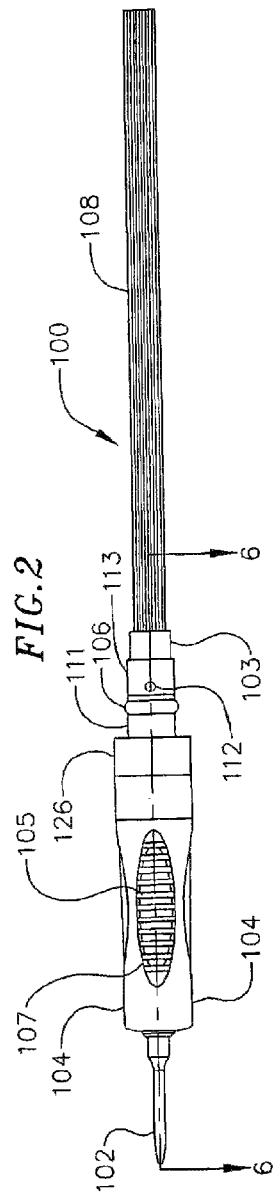
FIG. 2 is a top view of a dental tool insert having an integrated light source in an exemplary embodiment of the present invention.
Figure 3B:
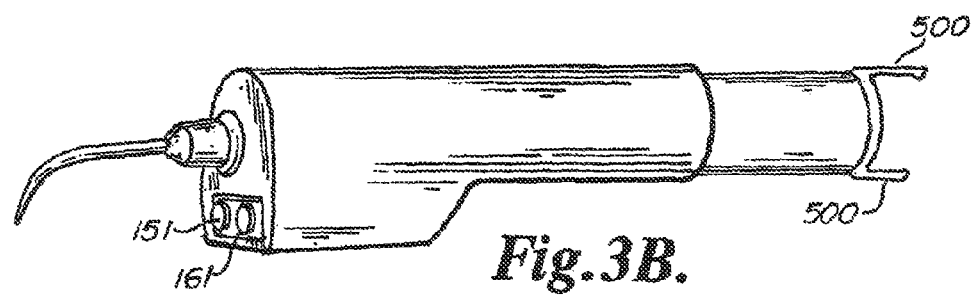
FIG. 3B illustrates the distal portion of the dental tool insert of FIG. 2 having more than one LED.
Figure 3D:
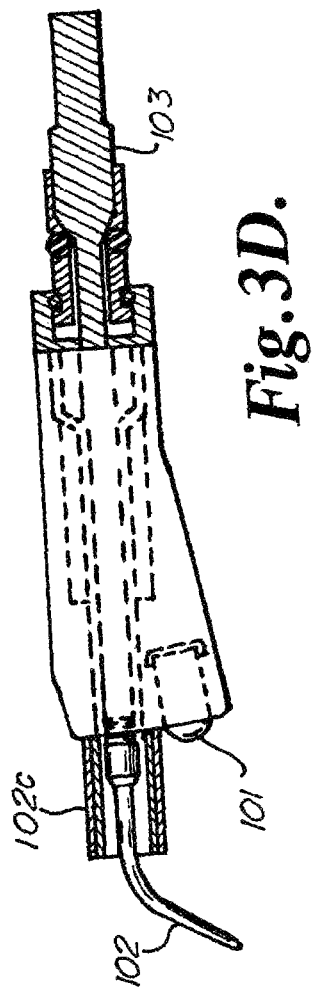
FIG. 3D is a cross-sectional view of FIG. 3C.

Referring now to FIGS. 2 and 3, the dental insert 100 includes the tip 102 at its distal end and an ultrasonic transducer 108 (first transducer) at its proximal end. The tip 102 is coupled to the transducer 108 via a connecting body 103, which may take the form of, for example, a shaft. The tip 102 may be permanently or removably attached to the connecting body 103. When removably attached, the tips 102 may be interchanged depending on the desired application. Further, the tip 102 may be disposed of, or steam autoclaved, or otherwise sterilized, after detaching it from the rest of the ultrasonic dental insert 100. For example, the tip 102 may be made using high temperature plastic such as a polyetherimide like ULTEM®, which is an amorphous thermoplastic polyetherimide; a polymeric alloy or Xenoy® resin, which is a composite of polycarbonate and polybutyleneterephthalate or Lexan® plastic, which is a copolymer of polycarbonate and isophthalate terephthalate resorcinol resin, all available from GE Plastics; a liquid crystal polymer; or any other suitable resin plastic or composite. The term "plastic" is used herein to generally designate synthetic polymeric material, such as resin.

The tip 102 may also be made of metal or metallic alloys such as stainless steel, which is particularly suitable when the tip is permanently attached to the insert 100. The attachment method may include any non-removable attachment such as soldering, welding, brazing, or the tip 102 may also be integrally formed as part of the connecting body 103.

The connecting body 103 may be made of any material suitable for transmitting ultrasonic vibrations such as stainless steel or other metals. The connecting body 103 is used to deliver ultrasonic vibrations generated by the transducer 108 to the tip 102 and for example, may be attached to the connecting body 103 by soldering, welding, laser welding and/or any other suitable method. For example, the joint between the connecting body 103 and the transducer 108 may be a brazed joint formed using a brazing compound, which includes cadmium free silver solder and high temperature brazing flux.

Figure 12:
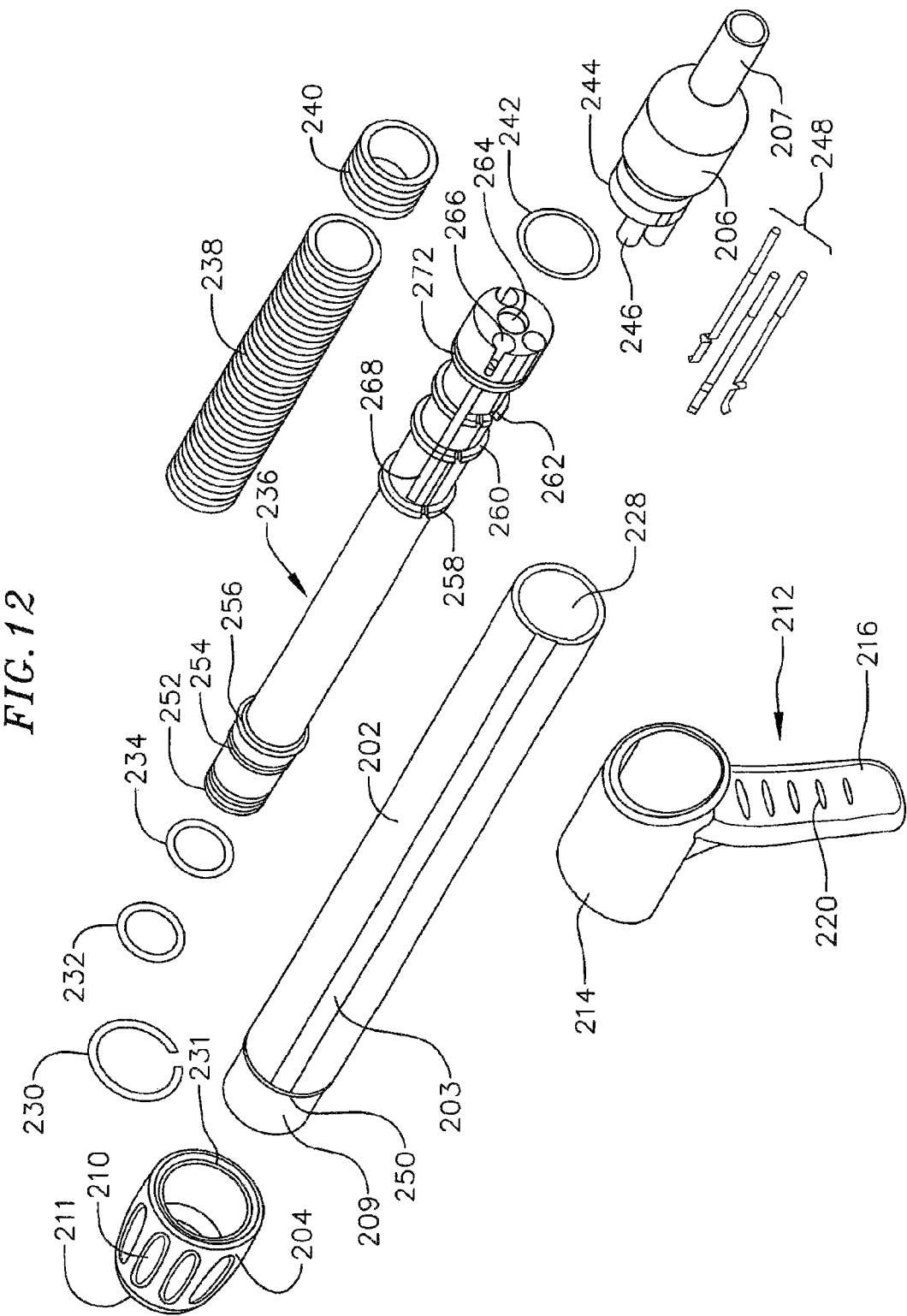
FIG. 12 is an exploded perspective view of the ultrasonic dental handpiece of FIG. 11.

When the connecting body 103 is also used to generate voltage in an illumination energy coil 238, as shown in FIG. 12, surrounding at least a portion of the connecting body 103, the connecting body 103 is, for example, made of a material that has magnetic permeability, and further for example, good magnetic permeability. By way of example, 17-4 PH stainless steel, and 420 stainless steel, while suitable for transmitting ultrasonic vibrations, are also mildly magnetic. Therefore, the connecting body 103 formed from 17-4 PH stainless steel may generate an ac voltage on the illumination energy coil 238 by moving rapidly (e.g., 25 kHz or faster) within the illumination energy coil 238 (not shown in FIGS. 2 and 3), which is mounted on an illumination energy bobbin 126. While only an end of the illumination energy bobbin 126 is shown in FIGS. 2 and 3, the illumination energy bobbin 126 actually envelops much of the connecting body 103 in the described embodiment as will be discussed in reference to FIGS. 6 and 7.

In one embodiment, the connecting body 103 has mounted thereon an annular retaining ring 111, which may also be made of metal such as stainless steel or other metals. The retaining ring 111 has a connecting portion 113, which has a generally cylindrical cavity formed therein for receiving a corresponding portion of the connecting body 103 in a force-fit relationship, or any other types of connections to be discussed below.

Figure 5:
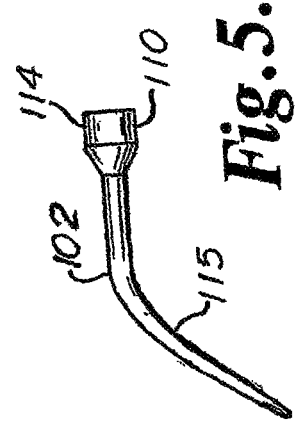
FIG. 5 illustrates the tip of FIG. 4, which has been rotated by approximately 90 degrees.
Figure 4:
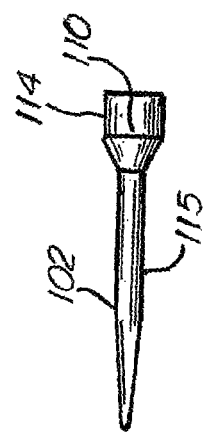
FIG. 4 illustrates a tip for the dental tool insert of FIG. 2.

Referring now to FIGS. 4 and 5, the tip has an elongated tapered portion 115, and a cylindrical interface portion 114 ("base"). The interface portion 114 may be adapted for removably connecting or disconnecting the tip 102 to the insert 100, as discussed below. It can be seen in FIG. 5 that the tapered portion 115 is curved to a certain degree. The tapered portion 115 has a circular cross section whose diameter decreases gradually from the end abutting the interface portion 114 ("the proximal end") to the other end of the tip ("the distal end"). The distal end is applied to the gum/teeth of the patient during the dental procedures. The degree of curve of the tapered portion 115 is chosen to better facilitate the functioning of the tip 102 on the tooth during operation of the dental tool 10 in a dental procedure.

In one embodiment, the curve in the tapered portion 115 may be towards the light source 101, i.e., towards the right side of the insert 100. In another embodiment, the curve in the tapered portion 115 may be away from the light source 101, i.e., towards the left side of the insert 100.

It can be seen in FIG. 4, that the cylindrical interface portion 114 has the linear groove 110 formed in the direction of the axis of the insert 100. The fluid traveling through the illumination bobbin 126 may exit through the linear groove 110 formed towards the distal end of the tip 102 in the described embodiment. This embodiment is a perspective view of the embodiment in FIG. 5, which shows a side view of the tip 102.

Figure 6D:
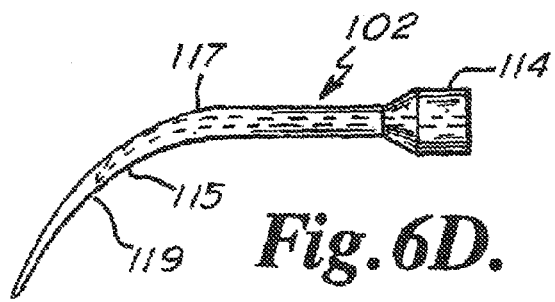
FIG. 6D illustrates an internal flow channel in the tip of the dental tool insert of FIG. 2 in an alternative embodiment of the present invention.
Figure 6A:
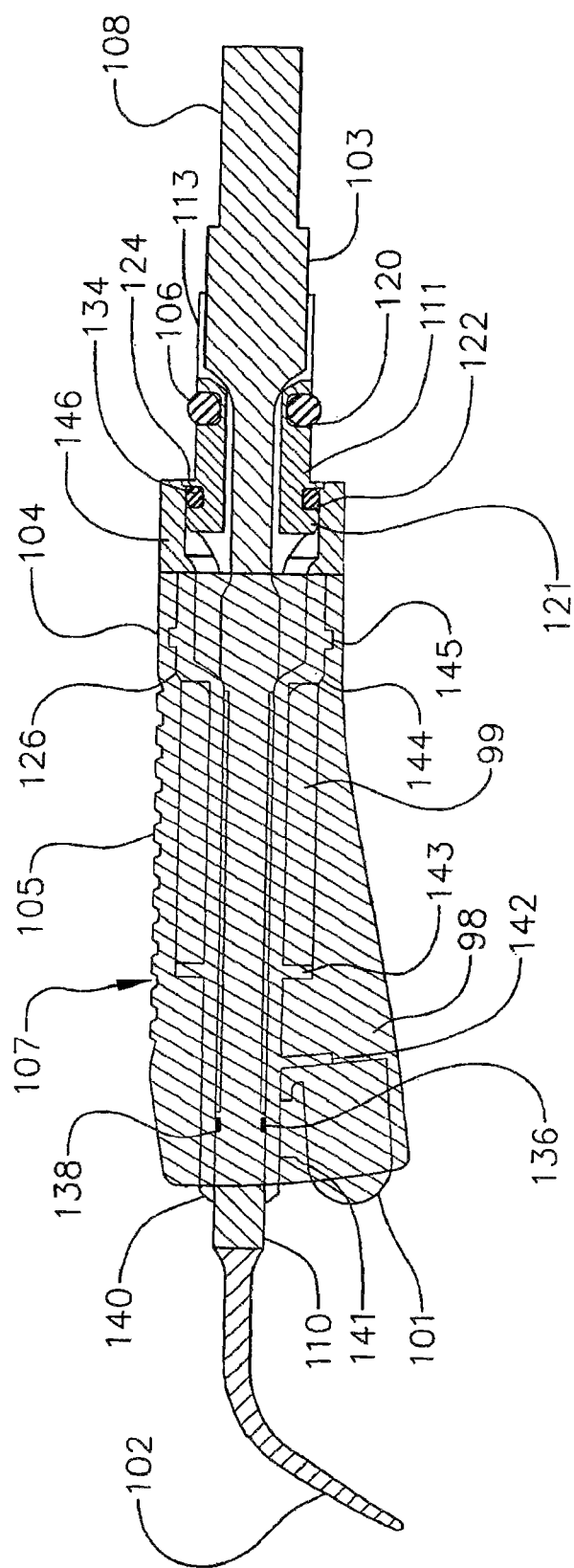
FIG. 6A is a cross-sectional view of the dental tool insert of FIG. 2, taken along the line 6-6.
Figure 6B:
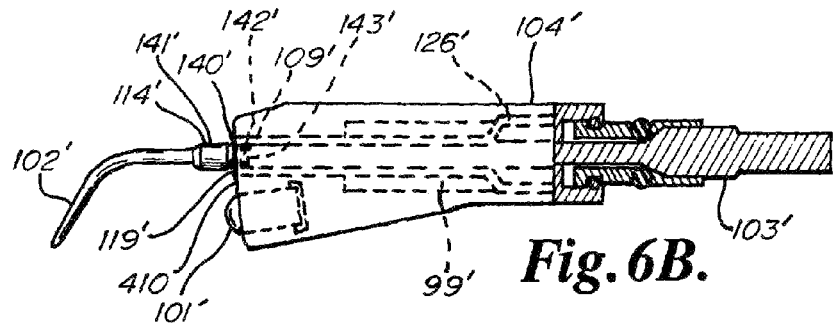
FIG. 6B is a partial cross-sectional view of a dental tool insert of another exemplary embodiment of the present invention.
Figure 6C:
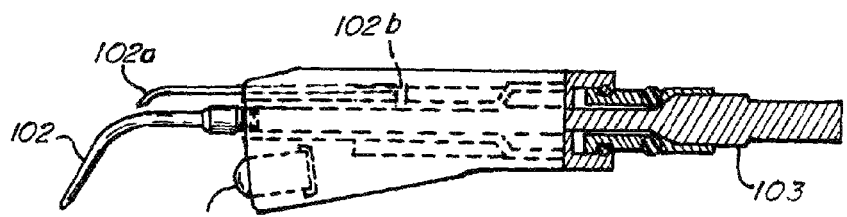
FIG. 6C is a partial cross-sectional view of the dental tool insert of FIG. 3A, including an external flow tube for delivering water to the tip in an alternative embodiment of the present invention.

In another embodiment, as exemplified in FIG. 6C, the insert 100 may include an external flow tube or pipe 102a, for example, in the form of a separate tube or pipe, for delivering water to the tip 102. The tube 102a may be disposed in such a way as to reduce spattering and produce an adhering coat of fluid on the tip 102. The external flow tube 102a may be supplied with water via an internal flow channel 102b, which interfaces with the fluid chamber inside the insert 100.

In other embodiments, the tip 102 may have an opening towards the distal end for enabling fluid to exit the insert 100, an example of this is shown in FIG. 3A or 6D. In this embodiment, the tip 102 may have a small passageway 117 therethrough for supplying water or other fluid to the region in the mouth being operated on.

In FIG. 6D, the insert tip 102 may utilize an internal flow channel 117, such as a small lumen or passage way 117 through a substantial length of its interior, which receives water from the internal fluid chamber within the insert 100 about the interface portion 114 and exits the tip 102 at the aperture 119 to deliver it to the working area.

The aperture 119 is eccentrically offset from the center axis of the tip 102 such that the passageway 117 is substantially parallel to the center axis of the tip 102 but displaced from said axis towards the distal end. In other examples, the insert 100 may have an opening at the end of its tip 102 which may have a small passage way 117 extending throughout the entire length such that water or any other liquid may exit the tip 102 at its distal point, depending on the type or function of the tip 102.

In yet another embodiment, as exemplified in FIGS. 3C and D, a sleeve 102c substantially surrounding a portion of the connecting body 103 to provide a gripping surface for the insert 100. The connecting body 103 includes an elongated region of reduced diameter proximal to the tip 102, and the sleeve 102c, may be positioned around and substantially filling the reduced diameter region of the connecting body 103, and covering at least portions of the tip 102, may be fitted over the tip 102 in such a manner that a small channel exits for water to pass through and guide towards the tip.

The sleeve 102c, may be in the form of, for example, an elongated elastomeric tube portion, and may also act to dampen noise generated by operation of the insert 100. The elastomeric material may include_an acrylic acid/acrylic ester copolymer such as iso-octylacrylate, having good vibration damping properties, or any of the materials described below for the handgrip. Some of these materials are also described in U.S. Pat. No. 5,118,562, the content of which is hereby incorporated by reference.

Further, an opening for applying the fluid to the mouth may instead be formed on the bobbin 126, as noted above, or the hand grip 104, as discussed further below.

The tip 102 may be in the form of a scaler, an endodontic dental file, a dental drill, or those useful for other periodontal treatments. The tip can also be made of metal or plastic, as discussed above. Some of them can also have a capability of delivering fluid and/or air.

The tip 102 may be formed as a single integrated piece with the connecting body 103, as mentioned before. In other embodiments, the tip 102 may have attached to the interface portion 114 a threaded portion for engaging a threaded opening formed on the connecting body 103. This is illustrated in FIG. 6B.

The ultrasonic dental insert 100' of FIG. 6B is substantially the same as the ultrasonic dental insert 100 of FIG. 6A, except that the tip 102' has attached to its interface portion 114' a threaded portion 109' for engaging a threaded receiving portion ("engagement portion" or "threaded tap") 119' formed at a distal end of a connecting body 103'. Using such threaded engagement 119', the tip 102' may be made removable. Such removability may allow the tip 102 to be a disposable tip 102' that is replaced after a single patient use. In still other embodiments, the removable tips may also be pressure fit into a corresponding opening on the connecting body 103'.

The replaceable tip 102', as shown in FIG. 6B, may be made of metal (e.g., stainless steel) or plastic (e.g., ULTEM®). Since the tip 102' has a very small diameter, it may be subject to breakage if too much ultrasonic vibrations are applied to it. On the other hand, if insufficient vibrations are applied, the ultrasonic dental tool may not work effectively. Therefore, the connecting body 103' and the tip 102' maybe designed such that a proper level of vibration is applied to the tip. Since a plastic tip is more likely to break than the metal tip, a shock absorbing mechanism may be used on the connecting body 103' to reduce the shock to the plastic tip 102', such as the elastomeric sleeve 102c described above in relationship to FIGS. 3C and D, or the O-rings 140' and 142', to be described below.

In one embodiment, the connecting body 103' has formed thereon the threaded tap 119' for screwing in the tip 102', as is shown in FIG. 6B. The word "tap" will refer hereinafter to a threaded opening formed at the distal end of the connecting body 103' for engaging the threaded portion 109'. The threaded portion 109' engages a corresponding thread on the inner surface of the threaded tap 119' such that the tip 102' is received by the connecting body 103'.

The connecting body 103' has formed surrounding the threaded tap 119' a pair of grooves 141' and 143' for seating O-rings 140' and 142', respectively. The O-rings absorb shock such that the vibrations "felt" by the tip 102 are reduced (i.e., dampened), thereby reducing the chance of breaking the plastic tip 102. In other embodiments, the connecting body may have only one or two or more O-rings mounted thereon for such shock absorption purposes. In still other embodiments, the threaded portion 109' may have a diameter that is substantially the same as the diameter of the interface portion 114', and the diameter of the threaded tap portion 119' may be correspondingly larger to receive the threaded portion 109'.

In one embodiment, the connecting body 103 or 103' may have mounted thereon an annular ring 111, which may also be made of a metal such as a stainless steel, as will be discussed further below.

Figure 2A:
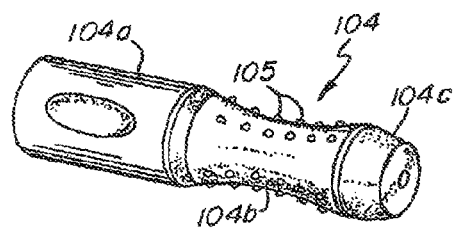
FIG. 2a is a perspective view of a multiple section handgrip for use in an exemplary embodiment of the present invention.

The housing or hand grip 104 may be made of high temperature resin. For example, the hand grip 104 may be fabricated using thermoplastic elastomer such as SANTOPRENE® available from the Monsanto Company, a polyvinylchloride polymer, a polyurethane foam or elastomer, a polyamide, natural or synthetic rubber, for example, elastomeric materials and may include, but not limited to, various copolymers or block copolymers (Kratons®) available from Kraton Polymers such as styrene-butadiene rubber or styrene isoprene rubber, EPDM (ethylene propylene diene monomer) rubber, nitrile (acrylonitrile butadiene) rubber, and the like, or those used in the construction of some tips, or any other suitable material that are moldable. In one embodiment, the handgrip 104 may be in one piece. In another embodiment, as shown in FIG. 2a, the handgrip 104 may be in multiple sections, for example, three sections, a proximal end section 104a and distal end section 104c of one material separated by a mid-section 104b of a different material. In one aspect, the three sections may only differ in color. In another aspect, the three sections may differ in hardness or softness. In yet another aspect, the three sections may differ in diameter or circumferential span. The sections may be co-molded or may be attached after forming.

In one embodiment, the hand grip 104 may be formed through injection molding after mounting the illumination energy coil 99 (to be discussed further below) and the light source 101 on the connecting body 103 via the illumination energy bobbin 126.

In other embodiments, the hand grip 104 may be a one-piece hand grip, which is mounted on the illumination energy bobbin 126 having a surrounding relationship with the connecting body 103 by sliding it over the illumination energy bobbin 126. In still other embodiments, multi-piece hand grips may be used. By way of example, a two-piece handgrip may be over-molded or ultrasonically welded together over the illumination energy bobbin 126. The one-piece or two-piece hand grip may be made of ULTEM®, SANTOPRENE®, Xenoy® or Lexan®, liquid crystal polymer or other suitable resin plastic, for example, as mentioned above, for example.

The hand grip 104 may have a generally cylindrical shape in one embodiment, to be fitted over the illumination energy bobbin 126 and connecting body 103, for securing the light source in place (e.g., through injection molding directly on the illumination energy bobbin 126). The hand grip 104 also has a slightly protruding portion 98 on one side at the end of which the light source 101 (e.g., LED) is disposed. In other embodiments, the retaining ring 111 may not be used, as will be discussed further below. Other embodiments of the handgrip 104 are also further described in detail below.

In one embodiment, along its outer surface on the other side of the slightly protruding portion 98, the hand grip 104 has a contour and has a slightly concave area 107, enabling it to be easily grasped by a dental practitioner. The hand grip 104 may also have formed thereon a plurality of bumps 105 (i.e., rounded or striped protrusions as shown in FIG. 2) on its external surface to further facilitate grasping of the device by a dental practitioner. Some may even be ergonomically designed. In the described embodiment, a linear groove (e.g., a passageway) 110 is formed on the tip 102 for delivering fluid (e.g., water) and/or air to the gum or tooth of the patient, as noted above.

More detail of the handgrip may be found in U.S. publication no. U.S. 2005/0142515 A1, entitled "Dental Tool Having A Hand Grip", the content of which is hereby incorporated by reference.

The transducer 108, as shown in FIGS. 2 and 3 may, for example, includes a stack of thin nickel plates arranged in parallel with respect to one another. Since the transducer 108 generates ultrasonic vibrations in the dental tool, the transducer 108 may also be referred to as a motor. In one embodiment the thin nickel plates may include 16 laminated nickel alloy strips, which are 90% nickel manganese (NiMn). The nickel plates may be joined together at both ends at a brazed joint using, for example, a brazing compound including cadmium free silver solder and high temperature brazing flux. The illustrated insert 100 is a magnetostrictive type insert 100 in which the nickel plates 108 can vibrate ultrasonically when a coil (e.g., coil 238, as shown in FIG. 12) in the handpiece 200 is energized using the electrical signals from the cable 12. In other embodiments, the ultrasonic dental insert 100 may use a piezoelectric transducer 108, as is common in Europe.

During operation, the stack of thin nickel plates 108, for example, vibrates at a frequency equal to the stack's natural frequency responsive to excitation induced by coils 268 of the handpiece 200. After the insert 100 is placed in the handpiece 200 and the electrical energy source 14 is powered on, the operator may manually tune the frequency of the electrical energy source until it reaches the resonance frequency, i.e., the natural frequency of the insert. Alternatively, auto-tune units may automatically lock on the insert resonance frequency once powered on. At this time, the stack begins vibrating. This vibration of the stack is amplified and transmitted to the tip 102 through the connecting body 103. Any means of amplification are contemplated. Ultrasonic inserts 100 may vibrate at frequencies of from about 20 KHz to about 50 KHz in general, and those used in the United States are typically designed to vibrate at frequencies of about 25 kHz or about 30 kHz.

In response to the ultrasonic vibration of the stack of thin nickel plates 108, the tip 102 and the connecting body 103 vibrates (e.g., rapid back and forth motion in the direction of the axis of the connecting body 103). By way of example, the motion in the direction of the axis may be between about 0.00125 centimeter (cm) to about 0.00375 cm depending on such factors as the vibration frequency, material used for the connecting body 103, the length of the connecting body 103, and the like.

As noted above, it is common in Europe to use a piezoelectric transducer to generate ultrasonic vibrations for a dental tool 10. During operation of such a dental tool, an electrical signal of an appropriate frequency is applied to a piezoelectric crystal. This electrical signal impresses a voltage across the crystal. In response to this voltage, the crystal expands and/or contracts and the expansion and/or contraction may be used to drive a tool tip.

As is known by one of skill in the art, the piezoelectric effect is reversible. Applying an appropriate stress to a piezoelectric crystal causes a voltage to appear across the crystal. This voltage, in turn, may be used to drive an electric current through an electrical load, such as a light emitting diode. Accordingly, in one embodiment of the invention shown in FIG. 13, a piezoelectric generator 312 is mechanically coupled to a connecting body adapted to support a tool tip 316 of a dental tool 300.

In operation, the ultrasonic generator 314 may be disposed within the magnetic field and vibrates in response to the alternation of the magnetic field. The vibrations of the ultrasonic generator 314 are mechanically coupled to the tip 316 and to the piezoelectric generator 312. This is exemplified further below in FIG. 13.

Figure 13:
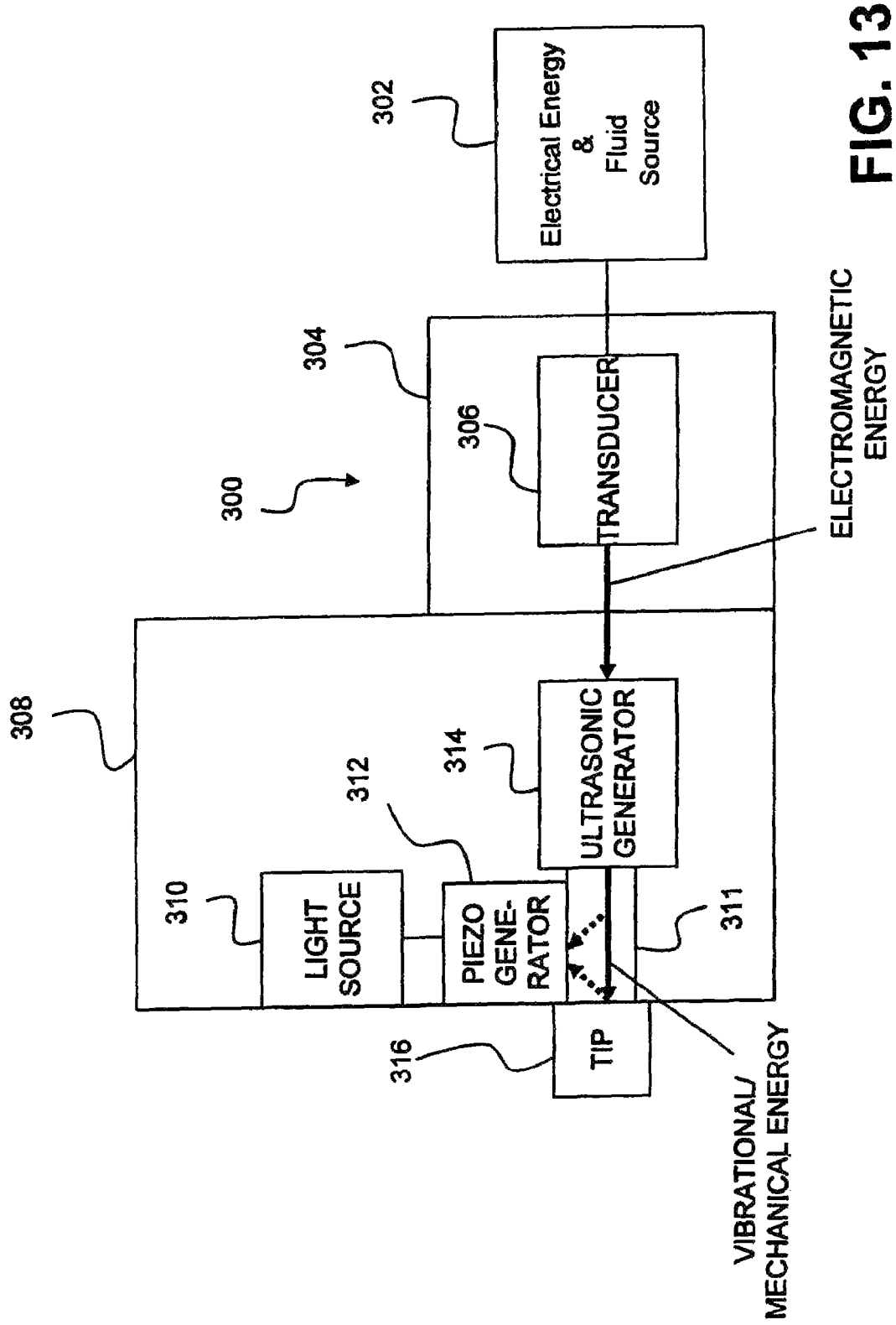
FIG. 13 is a block diagram of another example of an ultrasonic dental unit (or system) including a piezoelectric generator.

The piezoelectric generator 312 may include a piezoelectric body such as a quartz crystal, a Rochelle salt crystal, or a lead-zirconate-titanate (PZT) ceramic. Vibration of the tool tip 316 and/or a connecting body 311 induces an electrical voltage across the piezoelectric body. The electrical voltage drives a current through the light source 310, such as a light emitting diode, supported on the dental insert 308 of the dental tool 300. According to one aspect of the invention, light from the light source 310 is used to illuminate a work region near the tip 316 of the dental tool 300, as shown in FIG. 13.

Figure 7D:
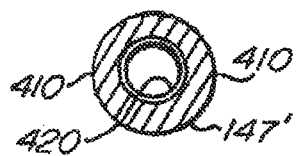
FIG. 7D shows another embodiment of a holder for the magnetic material or source.

Surprisingly, it is found that when the connecting body 103 or portions of the insert 100 is effectively magnetized, the output of the light source such as an LED 101 is sufficiently bright to be used on a workpiece. In one embodiment, when such mildly magnetic material is used for the connecting body 103, a magnetic source, such as a permanent magnet, a rare-earth magnet, or a magnetic field, may be used to initiate and/or also to re-establish proper magnetization of the metal connecting body 103 after autoclaving or exposure to unsuitable environment such as shock. When this re-magnetizing is done, the brightness of the light source, such as the LED 101, is increased by more than, for example, about 50% over that of a non-magnetized connecting body, or even over that of a mildly magnetized connecting body. The magnetic source 400 may be placed in close proximity to the connecting body 103 or the insert 100. For example, the magnetic source 400 may be embedded in the housing of the insert, as shown in FIG. 6A. In another exemplary embodiment, the magnetic source 410 may be removably coupled to the connecting body 103', as shown, for example in FIGS. 6B and 7D. As illustrated, FIGS. 6B and 7D show a magnetic source or material 410 in a substantially ring shaped holder 147', with the magnetic material or source 149' disposed on substantially opposite sides of the ring-shaped holder 147', the ring-shaped holder 147' having an internally threaded surface 420 that is adapted to receive an externally threaded portion of the connecting body 103'. In one aspect, the connecting body 103' may have a reduced diameter portion adapted to receive the ring-shaped holder 147' so that the holder 147' does not protrude from the connecting body 103'. In another aspect, the ring-shaped holder 147' may protrude from the connecting body 103'. One of skill in the art, however, will appreciate that many alternative modes of coupling such as a bayonet mount, a press fit, an adhesive mount, or a combination thereof, for example, would be possible and would fall within the scope of the invention.

In a further embodiment, at least a portion of the connecting body 103 and/or insert 100 may include a magnetic material or source 400, such as a permanent magnet, or a rare-earth magnet. A rare-earth metal, such as Neodymium-Boron, or Samarium-Cobalt, may be formed one at least a portion of the connecting body 103 towards the tip 102, for example, a holder 147' similar to that shown in FIG. 7D may be an integral part of the ultrasonic insert 100, or a portion of the insert, instead of a removable part, as shown in FIG. 7D. In one aspect, the holder 147' may not protrude from the rest of the connecting body 103'. In another aspect, the holder 147' may protrude from the connecting body 103'.

In addition, one of skill in the art would recognize that the shapes and locations of the magnetic materials or sources shown in FIGS. 6A and 6B are merely exemplary, and that many alternative locations would also fall within the invention scope, as long as the magnetic material or source is close to the tip 102 or 102'.

In one embodiment, the magnetic material or source 149 may be placed inside an appropriate holder, as exemplified in FIG. 7A, B, or C (to be further discussed below), to magnetize or to re-magnetize the insert 100 and tip 102 to allow the connecting body 103 to generate an electromagnetic field during operation of the insert 100 to power an attached light source 101 such as an LED. The holder may be in close proximity to the coil 126 inside the hand grip 104, as shown in FIG. 6B, that is used to generate the electromagnetic field that generates power to light the LED 101 connected to the insert 100. The presence of this magnetic material or source 400 may allow the connecting body 103 to retain its magnetic properties in an optimal manner even after exposure to heat or physical shock.

In another embodiment, the magnetic material or source 400 may be placed inside the hand grip 104 of the insert 100, and thus is in close proximity to the coil 99 inside the grip 104 that is used to generate the electromagnetic field, with one pole, for example, the north pole, of the magnetic source oriented in such a manner as to maximize that effect. This allows the connecting body 103 to retain its magnetic properties in an optimal manner even after exposure to heat or physical shock.

As noted, the connecting body 103 is used to transfer ultrasonic energy from an attached ultrasonic transducer 108 to the tip 102 of the connecting body 103, which may or may not be a detachable piece of the connecting body 103.

In the present invention, magnet materials or sources such as permanent magnets and rare earth magnets may be used. Iron, nickel, cobalt and some of the rare earths (gadolinium, dysprosium) exhibit a unique magnetic behavior which is called ferromagnetism because iron (ferric) is the most common and most dramatic example. Samarium and neodymium in alloys with cobalt or boron have also been used to fabricate very strong rare-earth magnets.

Ferromagnetic materials exhibit a long range ordering phenomenon at the atomic level which causes the unpaired electron spins to line up parallel with each other in a region called a domain. Within the domain, the magnetic field is intense, but in a bulk sample, the material may usually be unmagnetized because the many domains may themselves be randomly oriented with respect to one another. Ferromagnetism manifests itself in the fact that a small externally imposed magnetic field, say from a solenoid, may cause the magnetic domains to line up with each other and the material is said to be magnetized. The driving magnetic field is then increased by a large factor which is usually expressed as a relative permeability for the material.

Without wishing to be bound by a theory, it is surmised that some magnetic materials, for example those having low susceptibility or permeability (low tendency to become magnetized), low hysteresis, (low tendency to "remember their magnetic history"), or low remanence (the fraction of the saturation magnetization which is retained when the driving field is removed), may lose what little magnetic properties they have due to autoclaving, repeated cycling, and/or physical shock. This loss may also lead to loss in the ability of the device to convert mechanical energy to electrical energy, and hence, reduced brightness of the light source 102.

On the other hand, those materials having good susceptibility or permeability, good hysteresis, and high remanence, such as permanent magnets, some rare earth magnets, or ferromagnets, may be effective in initiating, maintaining, regenerating and/or increasing proper magnetization of the connecting body 103, and hence the brightness of the light source 102.

At the same time, all ferromagnets may also have a maximum temperature where the ferromagnetic property disappears as a result of thermal agitation. This temperature is called the Curie temperature. As long as the autoclaving temperature stays below this temperature, the magnetic properties may be maintained and the light source brightness is probably not affected. However, even below the Curie temperature, continual use and autoclaving may gradually reduce the magnetic property of the magnetic source 400, though the brightness of the light source 102 may remain in the useful range.

Autoclave in general is done above about 120° C. Therefore any magnetic source having a Curie temperature above that temperature is not likely to be affected by autoclaving.

Some rare earths, for example, gadolinium, have unusual superconductive properties. As little as 1 percent gadolinium may improve the workability and resistance of iron, chromium, and related alloys to high temperatures and oxidation. However, gadolinium has a Curie temperature at about room temperature, and thus may not be suitable for use as a portion of the connecting body 103, if autoclaving of such is to be customarily performed.

In one embodiment, if the magnetic material or source 400 used includes gadolinium or others having a low Curie temperature, it may be removable prior to autoclaving (as, for example, in the embodiment shown in FIG. 6B). The magnet, as long as it is in sufficiently close proximity to the connecting body 103 and/or the insert 100 during use, has value in initiating, re-magnetizing and maintaining proper magnetization of the connecting body 103.

In one aspect, the magnetic source may also be coated with a coating material for durability and/or corrosion resistance. The coating may include a polymeric material, a metallic coating, a non-metallic inorganic coating or combinations thereof. Examples of suitable polymeric material may be any that can be film forming either from solution, melt extruded or cast and may include those that are suitable for the tip 102 construction mentioned above. Examples of metallic coatings may include metallic nitride and carbide coatings such as titanium nitride, titanium carbide and so on. Examples of inorganic coatings may include ceramic coatings, diamond-like carbon coatings and the like.

Referring now to FIGS. 6A and 7, the connecting body 103 may also have formed thereon a circular groove 138 near its distal end. An O-ring 136 is seated in the groove 138. When the illumination energy bobbin 126 is mounted on the connecting body 103, the O-ring 136 provides a seal between the connecting body 103 and the illumination energy bobbin 126 so as to prevent undesired fluid leakage.

The illumination energy bobbin 126 may be formed as one-piece, and may be slid onto and snap/pressure fit to the connecting body and/or the retaining ring 111.

The retaining ring 111 has a generally cylindrical shape, and has formed thereon a connecting portion 113, which has a generally cylindrical cavity formed therein for receiving a corresponding portion of the connecting body 103, as is shown in FIG. 6A, in a force-fit relationship, or any other types of connections such as threaded connections, bayonet connections, and others. The retaining ring 111 is fixedly attached (e.g., snapped on) to the connecting body 103 such that it neither rotates nor moves laterally along the axis of the connecting body 103 during use.

The retaining ring 111 has an opening or two openings 112 formed thereon for receiving fluid from the handpiece 200, as noted before. When two openings are present, they are formed on opposite sides of the connecting portion 113. The fluid may exit through the linear groove 110 formed on the base 114 of the tip 102, as shown in FIG. 4 or 5. or may exit via any other mode, as shown in FIG. 3A, 6C, 3C or 3D, discussed above.

The retaining ring 111 has formed thereon, adjacent to the connecting portion 113, a circular groove 120 for seating the external O-ring 106.

At the distal end, the retaining ring 111 has formed thereon a pair of gripping elements 132 that face each other. Each gripping element has an end portion that protrudes inwardly toward the end portion of the other gripping element. The connecting body 103 has a pair of indentations 139 formed thereon for receiving the protruding end portions of the gripping elements such that the gripping elements 132 are snapped into the indentations 139. Thus engaged, the retaining ring 111 of the illustrated embodiment is locked to the connecting body 103, and neither rotates nor moves laterally with respect to the same. The retaining ring 111 has also formed thereon circular flanges 121, 124 and a circular groove 122. The circular groove 122 is for seating an O-ring 134.

In other embodiments, the retaining ring 111 may not be present.

More details of the retaining ring may be found in U.S. publication no. 2004/0126736 A1, entitled "Ultrasonic Dental Insert Having A Hand Grip Fitted To A Retaining Ring", the content of which is hereby incorporated by reference.

It can be seen in FIGS. 6A and 7 that the illumination energy coil 99 is wound around the illumination energy bobbin 126, which is mounted in a surrounding relationship with the connecting body 103. The bobbin 126, for example, may be made of high temperature plastic such as ULTEM® or any other suitable material mentioned above for the construction of the tip 102. The amount of voltage generated in the illumination energy coil 99 depends on such factors as the number of coil turns, the location of the illumination energy coil 99 with respect to the connecting body 103, the speed and frequency of the connecting body movement, the material used for the connecting body, and the like.

By way of example, when the illumination energy coil 99 may be made of, for example, an 18 gauge copper wire and have multiple turns and the connecting body 103 is, for example, made of 17-4 PH stainless steel, or 420 stainless steel, as mentioned above, the voltage signal having between about, for example, 1 and about 10 volts, more for example, about 1 to about 5 volts, peak-to-peak, may be generated with the vibration frequency of 25 kHz. Those skilled in the art would appreciate that the magnitude of the voltage generated will generally increase as the number of turns and/or the vibration frequency increase.

Further, in the illustrated embodiment, the voltage may increase as the illumination energy bobbin 126 (and the illumination energy coil 99) is mounted closer to the nodal point on the connecting body 103 than to the distal end where the tip 102 is attached to. The nodal point is where the magnitude of the longitudinal waves on the connecting body 103 is close to zero, and the longitudinal stress is at the maximum, and may in FIG. 6A be the location where the gripping elements 132 are attached to the connecting body 103 (i.e., the indentations 139).

Surprisingly, the presence of the magnetic material can increase the brightness of the light source to an extent that it render the location of mounting of the illumination bobbin 126 irrelevant, thus increasing the flexibility and robustness of manufacturing.

It can be seen in FIGS. 6A and 7 that the illumination energy bobbin 126 may have formed thereon, for example, a bracket 141 and a seat 142 for mounting the LED 101 thereon. Further, the illumination energy bobbin 126 has formed thereon a flange 143 and a generally cylindrical chamber 144, between which the illumination energy coil 99 is mounted. The generally cylindrical chamber 144 has formed thereon a flange 145. The illumination energy bobbin 126 also includes a ring section 146 attached to the chamber 144. The ring section 146 abuts the flange 121 of the retaining ring 111 when the ultrasonic dental insert 100 has been assembled.

Figure 7A:
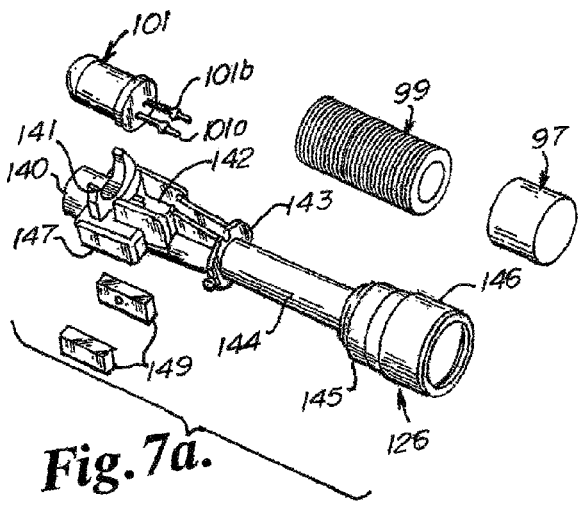
FIGS. 7A, 7B and 7C illustrate the inclusion of a light source, a transducer and magnetic elements to a portion of the dental tool insert of FIG. 2 in an exemplary embodiment of the present invention.
Figure 7B:
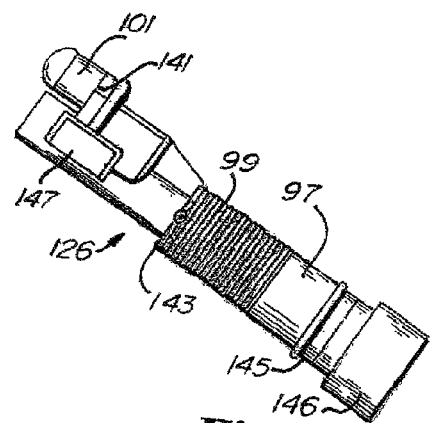
Figure 7C:
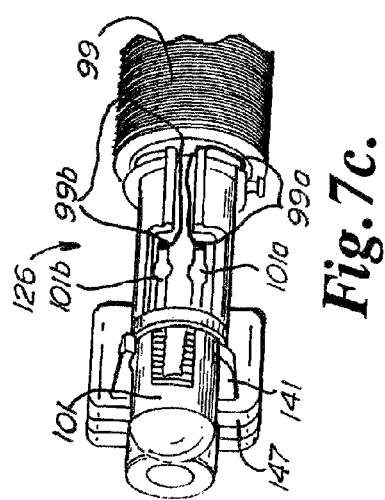

FIGS. 7A, 7B and 7C illustrate an exemplary embodiment of the illumination energy bobbin 126 of FIG. 7, showing the possible location of the magnetic material or source 400. As seen in the exploded view in FIG. 7A, the illumination energy bobbin 126 has formed thereon away from the ring section 146 a tube portion 140 which envelops the portion of the connecting body 103 near the tip 102 (not shown). In the described embodiment, the fluid enters the illumination energy bobbin 126 through the ring section 146, and exits the illumination energy bobbin 126 through the tube portion 140. The illumination energy coil 99 interfaces with the pins or electrodes 101a, 101b of the light source 101 through the ends of the coil 99a, 99b respectively, as illustrated in FIG. 7C, such that electrical energy may be passed from the illumination energy coil 99 to the light source 101. The illumination energy coil 99 may further have tape or other holding material 97, for example, disposed over at least a portion of the coil to maintain proper positioning and to prevent unwinding of the coil 99.

In accordance with the exemplary embodiment of the invention, the bobbin 126 further includes slots or other holding features 147 disposed near the light emitting circuitry, including the light source 101 and the illumination energy coil 99, as shown in FIG. 7A-C. In the present embodiment, the slots or holding features 147 may be for example, of a box-like shape, and may be adapted to receive and retain magnets or magnetic source 400 or elements 149 in proximity to the light emitting circuitry so as to initiate, increase, maintain or re-magnetize the insert 100 and tip 102 to allow the connecting body 103 to generate an electromagnetic field during operation of the insert 100 to power an attached light source 101 such as an LED. The holder 147 may be in close proximity to the coil 99 (not shown here) inside the grip 104 that is used to generate the electromagnetic field that generates power to light the LED 101 connected to the insert 100. The presence of this magnetic material or source 400 may allow the connecting body 103 to retain its magnetic properties in an optimal manner even after exposure to heat or physical shock, as described above.

Figure 8:
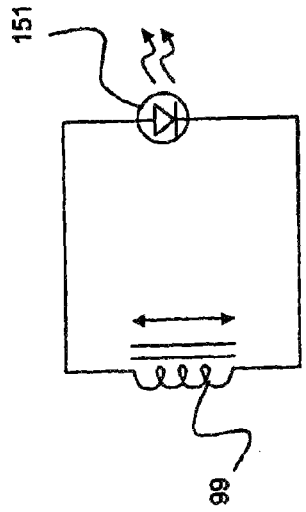
FIGS. 8, 9 and 10 illustrate light emitting circuitry of the integrated light source in exemplary embodiments of the present invention.

In the light emitting circuitry of FIG. 8, the light source may be an LED 151 connected in series with the illumination energy coil 99. Since the LED 151 emits light in response only to a voltage having single polarity, it emits light only half the time since the illumination energy coil 99 generates an ac voltage signal. However, since the LED 151 switches off and on at ultrasonic frequency (e.g., 25 kHz), such rapid switching of the LED is generally imperceptible to human eyes, and the LED 151 would appear to be continuously on. In other embodiments, the light source 101 may be any other suitable light emitting device such as an incandescent lamp (e.g., halogen light bulb).

Figure 9:
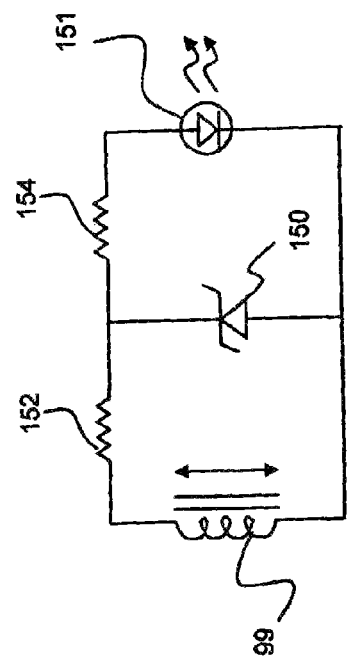

In the light emitting circuitry of FIG. 9, a zener diode 150 is connected in parallel to the LED 151 of the light source 101. A resistor 152 is connected between the illumination energy coil 99 and the zener diode 150, and a resistor 154 is connected between the zener diode 150 and the LED 151. The zener diode 150 clamps the voltage such that the voltage differential seen by the LED 151 does not rise over a certain predetermined voltage. This way, the brightness of the LED 151 may be kept substantially uniform even if the energy illumination coil 99 begins to generate higher voltage due to any fluctuation of the energy source 14 or other environmental conditions. By way of example, the zener diode 150 may clamp the voltage at 5 volts (V), such that the voltage seen by the LED 151 is no greater than 5V.

Figure 10:
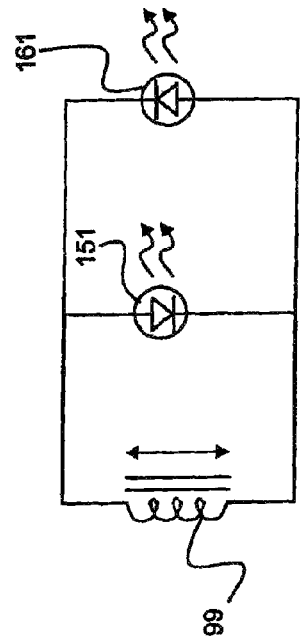

In FIG. 10, an LED 161 is connected in an anti-parallel relationship with the LED 151, such that they are connected in parallel but in opposite directions. This way, the LEDs 151 and 161 are alternately turned on in response to the ac voltage generated by the illumination energy coil 99. Since the ac voltage has an ultrasonic frequency (e.g., 25 kHz), the switching on and off of the LEDs 151 and 161 is imperceptible to human eyes, and therefore, both the LEDs 151 and 161 would appear to be on continuously. In other embodiments, the zener diode 150 may be used in parallel with each of the LEDs 151 and 161 in FIG. 9 so as to clamp the voltage for both the LEDs 151 and 161.

As noted, a light source 101 may be of a single LED, multiple LEDs or arrays. An examples is shown in FIG. 10 discussed above. The multiple LEDs 151, 161, may be arranged in any manner, for example, in a compact arrangement to minimize the overall size of the light source. Concentric arrays of LEDs (not shown) may also be used with arrangements, for example, controlled by a microprocessor, such that the areas of illumination may be varied as needed. A light transport apparatus may also be used so that the LEDs 151 may be located inside the connecting body to minimize the size of the protrusion of the tip 102. The transport apparatus may also include filters or reflectors to vary the size of the area of illumination. Light source 101 as used herein denotes the source of illumination such as the LED(s) 151, or the light transport apparatus, or combinations thereof.

The light source 101 may also be a single light source or a plurality of light sources, as shown in FIG. 4, for example, as 151 and 161, located substantially proximate to the tip 102, and connected to receive the voltage signal from the second transducer, such as the illumination coil 99 to generate light or to transport light. The plurality of light sources 101 may be spaced apart at varying distances from each other, but may still, for example, located proximate to the tip 102.

Figure 11:
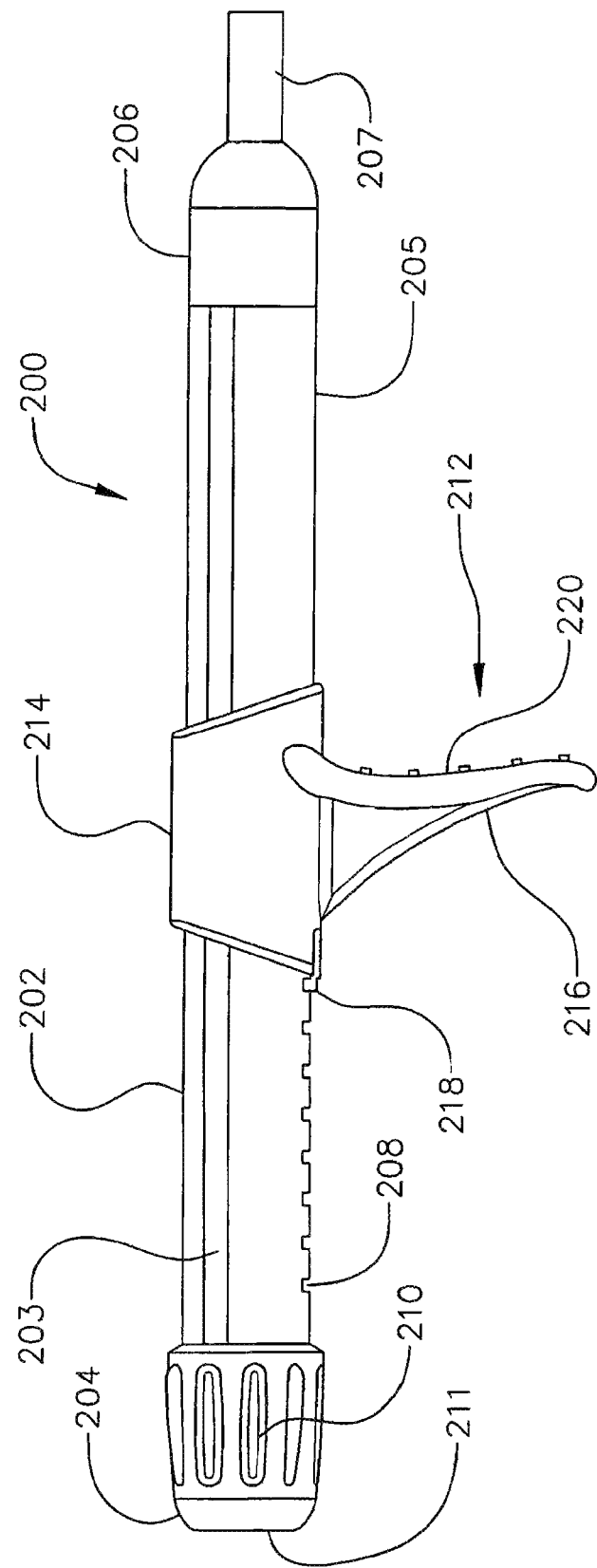
FIG. 11 is a side view of an ultrasonic dental handpiece that can be used with the ultrasonic dental insert of FIG. 2 to form an ultrasonic dental tool.

FIG. 11 illustrates a side view of the handpiece 200 that may receive the insert 100 as seen, for example, in FIG. 1. The handpiece 200 includes a body 202, a rotator head 204 and an interconnect 206. For handpieces 200 having a rotatable rotator head 204, for example, as shown here in FIG. 11, the O-ring 106 may engage the rotator head such that the ultrasonic dental insert 100 rotates together with the rotator head 204. For example, the rotator head 204 may be located at a distal end of the handpiece 200 and rotatably coupled to the rest of the handpiece 200. When the insert 100 is installed in the handpiece 200, the O-ring 106 is pressure fitted with an inner surface of the rotator head 204, such that the insert 100 rotates together with the rotator head 204. More details of the rotator head may be found in U.S. publication no. 2004/0126737 A1, entitled "Ultrasonic Dental Handpiece Having A Rotatable Head", the content of which is hereby incorporated by reference.

The interconnect 206 located at a proximal end of the handpiece 200 is coupled to a cable (e.g., the cable 12 of FIG. 1) for providing electrical signals as well as fluid (e.g., water) to the handpiece 200. The interconnect 206 may have a strain reliever 207 formed thereon to relieve strain between the interconnect 206 and the cable 12.

The rotator head 204 has a generally cylindrical shape, a hollow interior, and an opening at each end of the interior, which is used to receive the distal end of the body 202 of the handpiece 200 at one end and a dental insert 100 at the other end. For example, at its distal end, the rotator head 204 has formed thereon an opening 211 for receiving the ultrasonic dental insert 100.

The rotator head 204 has formed around its outer peripheral surface a plurality of indentations 210. Each indentation 210 has an elongated elliptical (or rectangular) shape with its major axis in the direction parallel to the central axis of the handpiece 200. The indentations 210 may facilitate grasping of the rotator head 204 by a dental practitioner to rotate it, for example, with respect to the body 202 of the handpiece 200

(e.g., using only one hand). In other embodiments, the rotator head 204 may have a number of protrusions formed thereon instead of the indentations 210.

The body 202 of the handpiece 200 has formed thereon a pair of grooves 203 that are substantially equidistant from the top and traverse substantially the whole length of the body 202. The grooves 203 are used to mount a hand grip 212 on the handpiece 200. The body 202 may also have formed thereon at its bottom near the distal end of the body 202 a plurality of substantially evenly spaced slots 208 that are used to keep the hand grip 212 from moving in the direction of the axis of the handpiece 200. The body 202 has also formed thereon at its bottom near the proximal end a groove 205 that is co-linear to the slots 208. The groove 205 engages the hand grip 212 together with the grooves 203 to keep the hand grip 212 from rotating about the central axis of the handpiece 200. In other embodiments, the grooves may not be used.

The hand grip 212 has an engagement portion 214, which has a generally cylindrical shape and a hollow interior. The engagement portion 214 is slipped onto the body 202 similar to a sleeve, and engages the body 202 such that the engagement portion envelops a portion of the body 202. The engagement portion has formed thereon a resilient cantilever portion 218, which may be used to engage one of the slots 208 on the body 202. The engagement portion 214 has attached to its bottom surface a handle 216, which may be used by a dental practitioner to hold the handpiece 200 during dental procedures. The handle 216 may also facilitate rotating of the rotator head 204 using one hand. The handle 216 has formed on its back surface a plurality of indentations or protrusions 220, which may be used to facilitate grasping by a dental practitioner. More details of this handgrip may be found in U.S. publication no. U.S. 2005/0142515 A1, entitled "Dental Tool Having A Hand Grip", the content of which is hereby incorporated by reference.

The handpiece 200 includes at least one coil 238 which may be mounted on a bobbin 236 (shown in FIG. 12) for providing the energy to the stack of nickel plates such that the nickel plates 108 vibrates at an ultrasonic frequency. The coil receives energy from the electrical energy & fluid source 14 through the cable 12 as shown in FIG. 1.

Referring now to FIG. 12, the handpiece 200 further includes a retainer ring 230, which may be made of metal, such as stainless steel. The retainer ring 230 is substantially circular in shape, but does not quite form a complete circle. The retainer ring 230 is flexible (resilient) and works as a spring in that the ends that are not connected together may be brought closer together by applying pressure, but they separate when the pressure is removed.

The rotator head 204 has formed on the inner surface near its proximal end a circular groove 231 that is used to engage the retainer ring 230. The retainer ring 230 may be installed in the circular groove 231, for example, by applying pressure on the retainer ring 230 to compress it, and releasing it once the retainer ring 230 has been aligned with the groove 231. Upon installation, the retainer ring 230 is locked to and is fixed with respect to the rotator head 204.

After locking the retainer ring 230 to the groove 231, the rotator head 204 may be coupled with the body 202 of the handpiece 200 by receiving the distal end of the body 202 into the rotator head opening at its proximal end. The body 202 has formed at its distal end an engagement portion 209, which has a radius that is smaller than the radius of the rest of the body 202. At a joint between the engagement portion 209 and the rest of the body 202 is formed a substantially circular groove 250 on an outer surface of the engagement portion 209. When the engagement portion 209 is inserted into the rotator head 204, the retainer ring 230 rotatably engages the groove 250 such that the rotator head 204 is rotatably coupled to the body 202. In other embodiments, the retaining ring 230 may be fixedly coupled to the body 202 and rotatably coupled to the rotator head 204.

The body 202 has an inner surface, which defines a hollow cavity 228 formed therethrough, into which a bobbin 236 is received. During a typical ultrasonic dental tool operation, fluid is pumped through the cable and the handpiece 200 to the tip 102 of the insert 100, as noted before. The vibrating tip 102 of the insert 100 breaks the fluid stream into a spray. The spray not only keeps the tip 102 cool, but also keeps the surface of the tooth cool and provides protection against tissue damage. The fluid path through the handpiece 200 (through the bobbin 236) is sealed such that no leakage occurs until the fluid stream exits from the insert 100 at the distal end through a fluid delivery channel, as discussed before. In some embodiments, the hollow cavity 228 may have more than one compartment through which air and water may be delivered, respectively. In an exemplary embodiment, the compartments may be stacked one above the other. The air is delivered via the lower compartment and water is delivered via the upper compartment so that instead of a stream, the air/water mixture becomes a fine mist which can be gentler on the teeth.

The bobbin 236, if present, has a generally cylindrical shape, and formed near its distal end a pair of circumferential grooves 252 and 254. The grooves 252 and 254 engage O-rings 232 and 234, respectively, and are used to prevent fluid from leaking out of the handpiece 200. For example, the O-ring 232 forms a water tight seal with the inner surface of the rotator head 204, while the O-ring 234 forms a water tight seal with the inner surface of the engagement portion 209.

The bobbin 236 has also formed thereon a pair of substantially circular flanges 256 and 258. A long coil 238 may be mounted on the bobbin 236 between the flanges 256 and 258. The bobbin 236 has also formed thereon a pair of substantially circular flanges 260 and 262 near its proximal end. A short coil 240 is mounted on the bobbin 236 between the circular flanges 260 and 262. The coils, 238, 240, for example, are made from insulated wires. In other embodiments, the coils, 238, 240, may have substantially the same length, or the longer coil may be mounted near the proximal end of the bobbin 236.

Near its proximal end, the bobbin 236 has formed thereon a circular groove 272 for seating an O-ring 242. By seating the O-ring 242 in the groove 272, a water tight seal is formed between the bobbin 236 and the inner surface of the body 202 such that the fluid does not leak from the handpiece 200.

The bobbin 236 has an inner surface, which defines a generally cylindrical cavity for transmitting fluid from the proximal end to the distal end, and has an opening 264 at its proximal end for receiving fluid into the cylindrical cavity. The bobbin 236 has also formed at its proximal end a plurality (e.g., three) of openings 266, which are used to receive plug pins 248 in the bobbin 236. The plug pins 248 are made of electrically conductive material such as copper. The bobbin 236, the body 202, the rotator head 204, the hand grip 212 and the casing for the interconnect 206 are made of a suitable synthetic polymeric material, such as those mentioned above that are suitable for the hand grip 104. For example, they may be fabricated using ULTEM®, which is an amorphous thermoplastic polyetherimide available from GE Plastics, liquid crystal polymer, as well as others disclosed above.

The bobbin 236 has also formed thereon a plurality of linear grooves 268 that are aligned with and extend from the respective openings 266 to the coils 238 and/or 240. The pins 248 installed, respectively, in the openings 266 and the grooves 268 are soldered and/or otherwise electrically connected to the coils 238 and/or 240, and are used to transmit electrical signals from the electrical energy & fluid and/or air source via the cable through the interconnect 206.

The interconnect 206 has also formed thereon a plurality (e.g., three) of elongated sockets 246 that engage the openings 266, respectively. The elongated sockets 246, for example, are formed on a connector portion 244 of the interconnect 206. The elongated sockets 246 have formed therein electrical contacts for making electrical connections with the plug pins 248, respectively. The electrical contacts are electrically connected at the other end with the wires in the cable 12, for example, to supply electrical energy to the coils 238 and 240, thereby energizing them.

In another embodiment of the invention, as exemplified in FIG. 13, the dental tool 300 includes a handpiece 304 and a dental insert 308. The handpiece 304 includes a transducer 306, which may be or includes a coil for energizing an ultrasonic generator 314 in the ultrasonic dental insert 308. The handpiece 304 receives electrical energy and fluid and/or gas (e.g., water) from an electrical energy, fluid and/or gas source 302. The handpiece 300, by way of example, may be substantially the same as the handpiece 200 of FIGS. 11 and 12. The dental insert 308 includes a light source 310 coupled to the piezoelectric generator 312. The electrical energy source 302 supplies an electrical signal to the transducer 306. The transducer 306 receives the electrical signal and generates an alternating magnetic field.

In operation, the ultrasonic generator 314 is disposed within the magnetic field and vibrates in response to the alternation of the magnetic field, as noted above. The vibrations of the ultrasonic generator 314 are mechanically coupled to the tip 316 and to the piezoelectric generator 312. The piezoelectric generator 312 generates an electrical current which is received by the light source 310. The light source 310 may be integrated with the dental insert 308, and may include two or more light sources, similar to that discussed before.

FIG. 14 illustrates a dental tool 300' having a handpiece 304' and a dental insert 308'. The dental tool 300' is coupled to an electrical energy, fluid and/or gas source 302', and operates in a similar manner as the dental tool 300 of FIG. 13, discussed above, except that the dental tool insert 308' includes a triboluminescent material 312' located near a tip 316' for providing illumination of the work region. A separate light source may not be needed as the triboluminescent material 312' emits light when stressed/deformed, e.g., by the vibrational energy generated by an ultrasonic generator 314' and transmitted via a connecting body 311'. The energy for the ultrasonic generator 314' is provided by a transducer 306' in the handpiece 304'.

FIG. 15 illustrates an example of illuminating a work region such as the mouth of a patient using the ultrasonic dental tool according to exemplary embodiments of the present invention. First, mechanical energy may be received at a generator (e.g., the illumination energy coil 99). The generator is mechanically supported by a tool handle (e.g., the handpiece 200). The tool handle is adapted to support an ultrasonic tool tip (e.g., the tip 102). Accordingly, an electrical energy is received at an input of an electromagnetic transducer (e.g., the coil 238) (320). A magnetic field is formed within the electromagnetic transducer (322). The magnetic field moves an electromechanical transducer, e.g., the ultrasonic transducer 108, either a magnetostrictive type or a piezoelectric type, using the magnetic field (324). By moving an input member, e.g., the connecting body 103, of the generator with the electromechanical transducer, the generator receives the mechanical energy (326). Moving the input member may involve reciprocating the input member at a frequency of from about 25 kHz to about 30 kHz.

The mechanical energy is converted to electromagnetic energy (328). To achieve this, a magnetized member, e.g., the connecting body 103, is moved past an electrical coil, which may include at least one helically-wound electrical conductor. Such moving of the magnetized member may include sliding the magnetized member in a substantially linear motion and/or rotating the magnetized member about a rotational axis. In other embodiments, the mechanical energy may be converted to electromagnetic energy by stressing a piezoelectric member to produce a voltage across the piezoelectric member as discussed above in reference to FIG. 13. In still other embodiments, triboluminescent material may be used to provide the illumination as discussed above in reference to FIG. 14.

At least a portion of the electromagnetic energy thus generated is used to illuminate the work region (330). When converting the mechanical energy to electromagnetic energy to illuminate the work region, an electrical energy may first be generated using the generator. Then the electrical signal is received through an electrical conductor at an input of a light source, which may be an LED or an incandescent lamp (e.g., halogen light bulb). Using the electrical energy, visible light is emitted from the light source. The generator, by way of example, may be disposed within the tool handle.

As shown in FIG. 15, with the illumination, a dental procedure may be performed using the tool handle (332). During the dental procedure, by way of example, a tooth is contacted with a tool tip, which is mechanically coupled to the tool handle, such that a surface of the tooth is disposed within the work region.

It will be appreciated by those of ordinary skill in the art that the present invention may be embodied in other specific forms without departing from the spirit or essential character hereof. The present description is therefore considered in all respects to be illustrative and not restrictive. The scope of the present invention is indicated by the appended claims, and all changes that come within the meaning and range of equivalents thereof are intended to be embraced therein.

I claim:
1. An ultrasonic dental insert comprising:
   a first transducer for generating ultrasonic vibrations;
   a connecting body having a proximal end and a distal end having a tip attached thereto, the proximal end attached to the first transducer so as to receive the ultrasonic vibrations therefrom and to transmit the ultrasonic vibrations toward the tip attached to the distal end, wherein the connecting body comprises a material having magnetic permeability;
   a second transducer disposed substantially proximate to the connecting body for generating a voltage signal in response to movement of a portion of the connecting body according to the ultrasonic vibrations due to the magnetic permeability of the connecting body;
   at least one rare earth magnet in close proximity to the connecting body, wherein the at least one rare earth magnet is mounted in a stationary position such that the connecting body moves relative to the at least one rare earth magnet; and
   at least one light source substantially proximate to the tip, said at least one light source being connected to and receiving the voltage signal from the second transducer to generate light.
2. The ultrasonic dental insert of claim 1, wherein the second transducer comprises a coil surrounding said portion of the connecting body, wherein the at least one rare earth magnet is mounted in a position such that it is not surrounded by the coil.

3. The ultrasonic dental insert of claim 2, wherein said at least one light source is an LED connected between a first end of the coil and a second end of the coil.

4. The ultrasonic dental insert of claim 3, further comprising a zener diode connected between the first end of the coil and the second end of the coil, such that the zener diode clamps voltage across the LED to a predetermined value.

5. The ultrasonic dental insert of claim 2 further comprising a bobbin on which the coil is mounted, said bobbin comprising a one-piece cylindrical structure for sliding onto said connecting body, and wherein said bobbin includes at least one holder formed integrally therewith, wherein said at least one rare earth magnet is disposed in said holder.

6. The ultrasonic insert of claim 5 further comprising at least two rare earth magnets contained within opposing holders positioned on opposite sides of the connecting body.

7. The ultrasonic dental insert of claim 2, further comprising a hand grip enveloping at least said portion of the connecting body.

8. The ultrasonic dental insert of claim 7, wherein the coil is at least partially disposed within the hand grip.

9. The ultrasonic dental insert of claim 8, further comprising a bobbin at least partially disposed within the hand grip in a surrounding relationship with said portion of the connecting body, wherein the coil, the at least one rare earth magnet and said at least one light source are mounted on the bobbin.

10. The ultrasonic dental insert of claim 9, further comprising a retaining ring snapped onto the connecting body, wherein the bobbin is fixedly attached to the retaining ring.

11. The dental insert of claim 9 wherein the bobbin includes a holder mounted thereon, and wherein the at least one rare earth magnet is disposed in the holder.

12. The ultrasonic dental insert of claim 7, wherein the hand grip is injection molded over at least said portion of the connecting body.

13. The ultrasonic dental insert of claim 7, wherein the at least one rare earth magnet is present inside the hand grip.

14. The ultrasonic dental insert of claim 1, wherein the first transducer comprises a magnetostrictive type or a piezoelectric type transducer.

15. The ultrasonic dental insert of claim 1, wherein the at least one rare earth magnet is permanently or removably attached to the dental insert.

16. The ultrasonic dental insert of claim 1, wherein the at least one rare earth magnet is contained within a holder proximate the connecting body.

17. The ultrasonic dental insert of claim 16 wherein said at least one rare earth magnet is adhesively attached to portions of the holder.

18. The ultrasonic dental insert of claim 16 further comprising at least two rare earth magnets contained within opposing holders positioned on opposite sides of the connecting body.

19. The dental insert of claim 1 wherein said tip comprises a tapered portion that is curved, and wherein said curve in said tapered portion is curved towards the light source or curved away from the light source.

20. The dental insert of claim 1 wherein the light source emits an output light, and wherein, during use, the brightness of the output light is increased by the at least one rare earth magnet.

21. The dental insert of claim 1 further comprising a handpiece for holding the ultrasonic dental insert and for providing electromagnetic energy to the first transducer to generate the ultrasonic vibrations, wherein the handpiece further comprises a retainer ring fixedly coupled to one of the body and the rotator head and rotatably coupled to the other of the body and the rotator head, such that the rotator head is rotatably coupled to the body.

* * * * *